(12) United States Patent
Heerding et al.

(10) Patent No.: US 7,625,890 B2
(45) Date of Patent: Dec. 1, 2009

(54) SUBSTITUTED IMIDAZO[4,5-C]PYRIDINE COMPOUNDS AS AKT INHIBITORS

(75) Inventors: Dirk A. Heerding, Collegeville, PA (US); Tammy J. Clark, Blair, NE (US); Jack Dale Leber, Collegeville, PA (US); Igor Safonov, Collegeville, PA (US)

(73) Assignee: SmithKline Beecham Corp., Philadelphia, PA (US)

( * ) Notice: Subject to any disclaimer, the term of this patent is extended or adjusted under 35 U.S.C. 154(b) by 0 days.

(21) Appl. No.: 11/823,415

(22) Filed: Jun. 27, 2007

(65) Prior Publication Data

US 2008/0076763 A1 Mar. 27, 2008

Related U.S. Application Data

(63) Continuation of application No. PCT/US2006/043513, filed on Nov. 9, 2006.

(60) Provisional application No. 60/826,928, filed on Sep. 26, 2006, provisional application No. 60/772,289, filed on Feb. 10, 2006, provisional application No. 60/735,955, filed on Nov. 10, 2005.

(51) Int. Cl.
C07D 471/04 (2006.01)
A61K 31/437 (2006.01)
A61K 31/4245 (2006.01)
A61P 35/04 (2006.01)
A61P 19/02 (2006.01)

(52) U.S. Cl. ........... 514/228.5; 514/234.5; 514/303; 546/118; 544/61; 544/118

(58) Field of Classification Search ........... 544/61, 544/118; 546/118; 514/228.5, 234.5, 303
See application file for complete search history.

(56) References Cited

U.S. PATENT DOCUMENTS

| | | |
|---|---|---|
| 4,336,257 A | 6/1982 | Baldwin |
| 5,958,950 A | 9/1999 | Padia et al. |
| 5,972,980 A | 10/1999 | Cornicelli et al. |
| 6,001,866 A | 12/1999 | Cornicelli et al. |
| 6,130,333 A | 10/2000 | Huang et al. |
| 6,211,367 B1 | 4/2001 | Cavalla et al. |
| 6,399,621 B1 | 6/2002 | Dusza et al. |
| 6,770,666 B2 | 8/2004 | Hashimoto et al. |
| 6,897,208 B2 | 5/2005 | Edwards et al. |
| 7,041,687 B2 | 5/2006 | Binch et al. |
| 7,112,600 B1 | 9/2006 | Hashimoto et al. |
| 2003/0220365 A1 | 11/2003 | Stewart et al. |
| 2004/0034037 A1 | 2/2004 | Harbeson et al. |
| 2005/0153978 A1 | 7/2005 | Alberti et al. |
| 2005/0176760 A1 | 8/2005 | Cezanne et al. |
| 2005/0182075 A1 | 8/2005 | Yuan |
| 2005/0197328 A1 | 9/2005 | Bailey et al. |
| 2006/0074102 A1 | 4/2006 | Cusack et al. |
| 2007/0004771 A1 | 1/2007 | Lee et al. |
| 2007/0043061 A1 | 2/2007 | Eberle et al. |
| 2007/0123561 A1 | 5/2007 | Lee et al. |
| 2007/0149561 A1 | 6/2007 | Dhanak et al. |
| 2008/0076763 A1 | 3/2008 | Heerding et al. |

FOREIGN PATENT DOCUMENTS

| | | |
|---|---|---|
| EP | 1702919 | 12/2004 |
| WO | WO01/13882 | 3/2001 |
| WO | WO02/32896 | 4/2002 |
| WO | WO2005/011700 | 2/2005 |
| WO | WO2005/037197 | 4/2005 |
| WO | WO2005/037198 | 4/2005 |
| WO | WO2005/046678 | 5/2005 |
| WO | WO2005/082890 A1 | 9/2005 |
| WO | WO2005/085227 | 9/2005 |
| WO | WO2006/113837 | 10/2006 |
| WO | WO2007/058852 | 5/2007 |
| WO | WO2007/058879 | 5/2007 |
| WO | WO2007/076423 | 7/2007 |
| WO | WO2008/058383 | 5/2008 |
| WO | WO2008/058603 | 5/2008 |
| WO | WO2008/098104 | 8/2008 |
| WO | WO2008/098105 | 8/2008 |

OTHER PUBLICATIONS

Vippgunta et. al., Advanced Drug Delivery Reviews, 2001, 48, 3-26.*
STN structure search, downloaded Feb. 1, 2008, pp. 29-31.*
Anderson, et al., J. Org. Chem., 2003, vol. 68, pp. 9563-9573.
Abraham, Current Opinion of Imm., 1996, vol. 8, pp. 412-416.
Ashby, Current Opinion in Lipidology, 1998, vol. 9, No. 2, pp. 99-102.
Bolen, et al., Annu. Rev. Immunol., 1997, vol. 15, pp. 371-404 and table of contents.
Brodt, et al., Biochemical Pharm., 2000, vol. 60, pp. 1101-1107.
Bruns, et al., Cancer Research, 2000, vol. 60, pp. 2926-2935.
Canman, et al., Oncogene, 1998, vol. 17, pp. 3301-3308.
Chen, et al., Cancer Research, 1998, vol. 58, pp. 1965-1971.
Choi, et al., Cell Transplantation, 2002, vol. 11, pp. 359-368.
Forastiere, Seminars in Oncology, 1993, vol. 20. No. 4, Suppl. 3, pp. 56-60.

(Continued)

*Primary Examiner*—James O Wilson
*Assistant Examiner*—Susanna Moore
(74) *Attorney, Agent, or Firm*—Wayne J. Dustman; Edward R. Gimmi; Charles M. Kinzig

(57) ABSTRACT

Invented are novel 1H-imidazo[4,5-c]pyridin-2-yl compounds, the use of such compounds as inhibitors of protein kinase B activity and in the treatment of cancer and arthritis.

13 Claims, No Drawings

OTHER PUBLICATIONS

Holmes, et al., J. of the Nat'l Cancer Inst., 1991, vol. 83, No. 24, pp. 1797-1805.
Jackson, Int. J. Biochem. Cell Biol., 1997, vol. 29, No. 7, pp. 935-938.
Kath, Exp. Opin. Ther. Patents, 2000, vol. 10, No. 6, pp. 803-818.
Kearns, et al., Seminars in Oncology, 1995, vol. 22, No. 3, suppl. 6, pp. 16-23.
Kerr and Workman, New Molecular Targets for Cancer Chemotherapy, 1993, CRC Press, Cancer Research Campaign Beatson Laboratories, University of Glasgow, UK. Table of Contents, pp. 67-79.
Kelley, et al., J. Med. Chem., 1995, vol. 38, pp. 4131-4134.
Kingston, et al., Studies in Organic Chemsitry, 1986, vol. 26., pp. 219-235.
Kitada,e t al., Antisense Research & Dev., 1994, vol. 4, pp. 71-79.
Kumar, The J. of Biol. Chem., 1981, vol. 256, No. 20, pp. 10435-10441.
Lackey, et al., Bioorg. & Med. Chem. Letters, 2000, vol. 10, pp. 223-226.
Larock, Comprehensive Organic Transformations, Published 1989, Book Cover & Table of Contents.
Markman, The Yale J. of Biol. & Medicine, 1991, vol. 64, pp. 583-590.
Martinez-Lacaci, et al., Int. J. Cancer, 2000, Vol. 88, pp. 44-52.
Massague, et al., Cancer Surveys, 1996, ol. 27, pp. 41-64.
McGuire, et al., Annals of Internal Medicine, 1989, vol. 111, pp. 273-279.
Mitsunobu, Synthesis, The Use of Diethyl Azadicarboxylate and Triphenylphosphine, 1981, pp. 1-28.
Oliff, Biochemica et Biophysica Acta, 1999, vol. 1423, pp. C19-C30.
Reilly, et al., Cancer Research, 2000, vol. 60, pp. 3569-3576.
Rosania, et al., Exp. Opin. Ther. Patents, 2000, vol. 10, No. 2, pp. 215-230.
Sanchez, et al., J. Hetercyclic Chem., 1993, vol. 30, pp. 855-859.
Schreiber, et al., Science, 1986, vol. 232, pp. 1250-1253.
Scharosky, et al., J. Biomed Sci, 2000, vol. 7, pp. 292-298.
Schiff, et al., Nature, 1979, vol. 277, pp. 665-667.
Schiff, et al., Proc. Natl. Acad. Sci., 1980, vol. 77, No. 3, pp. 1561-1565.
Shawver, et al., DDT, 1997, vol. 2, No. 2, pp. 51-63.
Sinha, et al., J. of Hematotherapy & Stem Cel Research, 1999, vol. 8, pp. 465-480.
Smithgall, et al., J. of Pharm. & Toxicol. Methods, 1995, vol. 34, pp. 125-132.
Wani, et al., Chem. & Life Sciences Lab, NC, 1971, pp. 2325-2327.
Waters, et al., J. of Clinical Oncology, 2000, vol. 18, No. 9, pp. 1812-1823.
Yamamoto, et al., J. Biochem, 1999, vol. 126, pp. 799-803.
Yen, et al., Oncogene, 2000, vol. 19, pp. 3460-3469.
Zhong, et al., Cancer Research, 2000, vol. 60, pp. 1541-1545.
Nawwar, et al., Anales De Quimica, 1993, vol. 89, No. 3, pp. 375-378.
Li, et al., Current Topics in Med. Chem., 2002 vol. 2, pp. 939-971.
Olesen, et al., J. Med. Chem., 2003, vol. 46, pp. 3333-3341.
Bamford, et al., Bioorganic & Med. Chem. Letters, vol. 15, pp. 3407-3411.
Barraclough, et al., Archiv der Pharmazie, 1990, vol. 323, pp. 507-512.
Yutilov, et al., Khimiya Geterosiklicheskikh Soedinenii, 1989, vol. 7, pp. 940-947. (org. & translation).
PCT/US2006/043518 filed Nov. 9, 2006.
PCT/US2006/043617 filed Nov. 9, 2006.
PCT/US2006/062453 filed Nov. 9, 2006.
Wadler, et.al., *Proc. Am. Soc. Clin. Oncol.*, (20), 2001, abstract.
Hassner & Stumer, *Organic Syntheses Based on Name Reactions and Unnamed Reactions*, Oxford, New York: Pergamon; Table of Contents (1994).

* cited by examiner

//\# SUBSTITUTED IMIDAZO[4,5-C]PYRIDINE COMPOUNDS AS AKT INHIBITORS

This application is a continuation of International Application No. PCT/US2006/043513 filed Nov. 9, 2006, which claims the benefit of U.S. Provisional Application Nos. 60/826,928 filed Sep. 26, 2006, 60/772,289 filed Feb. 10, 2006 and 60/735,955 filed Nov. 10, 2005.

FIELD OF THE INVENTION

This invention relates to novel 1H-imidazo[4,5-c]pyridin-2-yl compounds, the use of such compounds as inhibitors of protein kinase B (hereinafter PKB/Akt, PKB or Akt) activity and in the treatment of cancer and arthritis.

BACKGROUND OF THE INVENTION

The present invention relates to 1H-imidazo[4,5-c]pyridin-2-yl containing compounds that are inhibitors of the activity of one or more of the isoforms of the serine/threonine kinase, Akt (also known as protein kinase B). The present invention also relates to pharmaceutical compositions comprising such compounds and methods of using the instant compounds in the treatment of cancer and arthritis (Liu et al. *Current Opin. Pharmacology* 3:317-22 (2003)).

Apoptosis (programmed cell death) plays essential roles in embryonic development and pathogenesis of various diseases, such as degenerative neuronal diseases, cardiovascular diseases and cancer. Recent work has led to the identification of various pro- and anti-apoptotic gene products that are involved in the regulation or execution of programmed cell death. Expression of anti-apoptotic genes, such as Bcl2 or Bcl-$x_L$, inhibits apoptotic cell death induced by various stimuli. On the other hand, expression of pro-apoptotic genes, such as Bax or Bad, leads to programmed cell death (Adams et al. *Science*, 281:1322-1326 (1998)). The execution of programmed cell death is mediated by caspase-1 related proteinases, including caspase-3, caspase-7, caspase-8 and caspase-9 etc (Thornberry et al. *Science,* 281:1312-1316 (1998)).

The phosphatidylinositol 3'-OH kinase (PI3K)/Akt/PKB pathway appears important for regulating cell survival/cell death (Kulik et al. *Mol. Cell. Biol.* 17:1595-1606 (1997); Franke et al, *Cell,* 88:435-437 (1997); Kauffmann-Zeh et al. *Nature* 385:544-548 (1997) Hemmings *Science,* 275:628-630 (1997); Dudek et al., *Science,* 275:661-665 (1997)). Survival factors, such as platelet derived growth factor (PDGF), nerve growth factor (NGF) and insulin-like growth factor-1 (IGF-I), promote cell survival under various conditions by inducing the activity of PI3K (Kulik et al. 1997, Hemmings 1997). Activated PI3K leads to the production of phosphatidylinositol (3,4,5)-triphosphate (PtdIns (3,4,5)-P3), which in turn binds to, and promotes the activation of, the serine/threonine kinase Akt, which contains a pleckstrin homology (PH)-domain (Franke et al *Cell,* 81:727-736 (1995); Hemmings *Science,* 277:534 (1997); Downward, *Curr. Opin. Cell Biol.* 10:262-267 (1998), Alessi et al., *EMBO J.* 15: 6541-6551 (1996)). Specific inhibitors of PI3K or dominant negative Akt/PKB mutants abolish survival-promoting activities of these growth factors or cytokines. It has been previously disclosed that inhibitors of PI3K (LY294002 or wortmanin) blocked the activation of Akt/PKB by upstream kinases. In addition, introduction of constitutively active PI3K or Akt/PKB mutants promotes cell survival under conditions in which cells normally undergo apoptotic cell death (Kulik et al. 1997, Dudek et al. 1997).

Analysis of Akt levels in human tumors showed that Akt2 is overexpressed in a significant number of ovarian (J. Q. Cheung et al. *Proc. Natl. Acad. Sci. U.S.A.* 89:9267-9271 (1992)) and pancreatic cancers (J. Q. Cheung et al. *Proc. Natl. Acad. Sci. U.S.A.* 93:3636-3641 (1996)). Similarly, Akt3 was found to be overexpressed in breast and prostate cancer cell lines (Nakatani et al. *J. Biol. Chem.* 274:21528-21532 (1999). It was demonstrated that Akt-2 was over-expressed in 12% of ovarian carcinomas and that amplification of Akt was especially frequent in 50% of undifferentiated tumors, suggestion that Akt may also be associated with tumor aggressiveness (Bellacosa, et al., *Int. J. Cancer,* 64, pp. 280-285, 1995). Increased Akt1 kinase activity has been reported in breast, ovarian and prostate cancers (Sun et al. *Am. J. Pathol.* 159: 431-7 (2001)).

The tumor suppressor PTEN, a protein and lipid phosphatase that specifically removes the 3' phosphate of PtdIns (3,4,5)-P3, is a negative regulator of the PI3K/Akt pathway (Li et al. *Science* 275:1943-1947 (1997), Stambolic et al. *Cell* 95:29-39 (1998), Sun et al. *Proc. Natl. Acad. Sci. U.S.A.* 96:6199-6204 (1999)). Germline mutations of PTEN are responsible for human cancer syndromes such as Cowden disease (Liaw et al. *Nature Genetics* 16:64-67 (1997)). PTEN is deleted in a large percentage of human tumors and tumor cell lines without functional PTEN show elevated levels of activated Akt (Li et al. supra, Guldberg et al. *Cancer Research* 57:3660-3663 (1997), Risinger et al. *Cancer Research* 57:4736-4738 (1997)).

These observations demonstrate that the PI3K/Akt pathway plays important roles for regulating cell survival or apoptosis in tumorigenesis.

Three members of the Akt/PKB subfamily of second-messenger regulated serine/threonine protein kinases have been identified and termed Akt1/PKBα, Akt2/PKBβ, and Akt3/PKBγ respectively. The isoforms are homologous, particularly in regions encoding the catalytic domains. Akt/PKBs are activated by phosphorylation events occurring in response to PI3K signaling. PI3K phosphorylates membrane inositol phospholipids, generating the second messengers phosphatidyl-inositol 3,4,5-trisphosphate and phosphatidylinositol 3,4-bisphosphate, which have been shown to bind to the PH domain of Akt/PKB. The current model of Akt/PKB activation proposes recruitment of the enzyme to the membrane by 3'-phosphorylated phosphoinositides, where phosphorylation of the regulatory sites of Akt/PKB by the upstream kinases occurs (B. A. Hemmings, *Science* 275:628-630 (1997); B. A. Hemmings, *Science* 276:534 (1997); J. Downward, *Science* 279:673-674 (1998)).

Phosphorylation of Akt1/PKBα occurs on two regulatory sites, $Thr^{308}$ in the catalytic domain activation loop and on $Ser^{473}$ near the carboxy terminus (D. R. Alessi et al. *EMBO J.* 15:6541-6551 (1996) and R. Meier et al. *J. Biol. Chem.* 272: 30491-30497 (1997)). Equivalent regulatory phosphorylation sites occur in Akt2/PKBβ and Akt3/PKBγ. The upstream kinase, which phosphorylates Akt/PKB at the activation loop site has been cloned and termed 3'-phosphoinositide dependent protein kinase 1 (PDK1). PDK1 phosphorylates not only Akt/PKB, but also p70 ribosomal S6 kinase, p90RSK, serum and glucocorticoid-regulated kinase (SGK), and protein kinase C. The upstream kinase phosphorylating the regulatory site of Akt/PKB near the carboxy terminus has not been identified yet, but recent reports imply a role for the integrin-linked kinase (ILK-1), a serine/threonine protein kinase, or autophosphorylation.

Inhibition of Akt activation and activity can be achieved by inhibiting PI3K with inhibitors such as LY294002 and wortmanin. However, PI3K inhibition has the potential to indiscriminately affect not just all three Akt isozymes but also other PH domain-containing signaling molecules that are dependent on PdtIns(3,4,5)-P3, such as the Tec family of tyrosine kinases. Furthermore, it has been disclosed that Akt can be activated by growth signals that are independent of PI3K.

Alternatively, Akt activity can be inhibited by blocking the activity of the upstream kinase PDK1. The compound UCN-01 is a reported inhibitor of PDK1. *Biochem. J.* 375(2):255 (2003). Again, inhibition of PDK1 would result in inhibition of multiple protein kinases whose activities depend on PDK1, such as atypical PKC isoforms, SGK, and S6 kinases (Williams et al. *Curr. Biol.* 10:439-448 (2000).

Small molecule inhibitors of Akt are useful in the treatment of tumors, especially those with activated Akt (e.g. PTEN null tumors and tumors with ras mutations). PTEN is a critical negative regulator of Akt and its function is lost in many cancers, including breast and prostate carcinomas, glioblastomas, and several cancer syndromes including Bannayan-Zonana syndrome (Maehama, T. et al. *Annual Review of Biochemistry*, 70: 247 (2001)), Cowden disease (Parsons, R.; Simpson, L. *Methods in Molecular Biology* (Totowa, N.J., United States), 222 (*Tumor Suppressor Genes, Volume* 1): 147 (2003)), and Lhermitte-Duclos disease (Backman, S. et al. *Current Opinion in Neurobiology*, 12(5): 516 (2002)). Inhibition of Akt has also been implicated in the treatment of leukemias, (J. C. Byrd, S. Stilgenbauer and I. W. Flinn "Chronic lymphocytic leukemia." Hematology/the Education Program of the American Society of Hematology. American Society of Hematology. Education Program (2004), 163-83). Akt3 is up-regulated in estrogen receptor-deficient breast cancers and androgen-independent prostate cancer cell lines and Akt2 is over-expressed in pancreatic and ovarian carcinomas. Akt1 is amplified in gastric cancers (Staal, *Proc. Natl. Acad. Sci. USA* 84: 5034-7 (1987) and upregulated in breast cancers (Stal et al. *Breast Cancer Res.* 5: R37-R44 (2003)). Therefore a small molecule Akt inhibitor is expected to be useful for the treatment of these types of cancer as well as other types of cancer. Akt inhibitors are also useful in combination with further chemotherapeutic agents.

It is an object of the instant invention to provide novel compounds that are inhibitors of Akt/PKB.

It is also an object of the present invention to provide pharmaceutical compositions that comprise a pharmaceutical carrier and compounds useful in the methods of the invention.

It is also an object of the present invention to provide a method for treating cancer that comprises administering such inhibitors of Akt/PKB activity.

It is also an object of the present invention to provide a method for treating arthritis that comprises administering such inhibitors of Akt/PKB activity.

SUMMARY OF THE INVENTION

This invention relates to novel compounds of Formula (I):

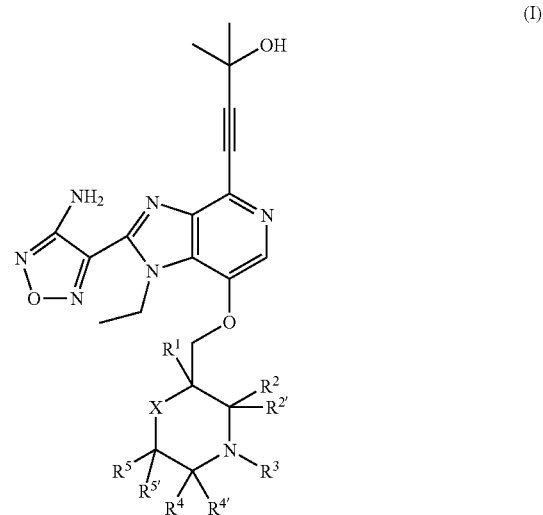

wherein:
X is absent or selected from the group consisting of: O, S and $CR^{20}R^{21}$, where $R^{20}R^{21}$ are independently selected from: hydrogen, fluorine, cyclopropyl, substituted cyclopropyl, cyclobutyl, substituted cyclobutyl, cyclopentyl, substituted cyclopentyl, —$C_1$-$C_4$alkyl, and substituted —$C_1$-$C_4$alkyl,
or $R^{20}R^{21}$ taken together with the carbon to which they are attached form cyclopropyl, substituted cyclopropyl, cyclobutyl, substituted cyclobutyl, cyclopentyl or substituted cyclopentyl;

$R^2R^{2'}$ are independently selected from: hydrogen, fluorine, cyclopropyl, substituted cyclopropyl, cyclobutyl, substituted cyclobutyl, cyclopentyl, substituted cyclopentyl, —$C_1$-$C_4$alkyl, and substituted —$C_1$-$C_4$alkyl,
or $R^2R^{2'}$ taken together with the carbon to which they are attached form cyclopropyl, substituted cyclopropyl, cyclobutyl, substituted cyclobutyl, cyclopentyl or substituted cyclopentyl;

$R^3$ is selected from the group consisting of: hydrogen, cyclopropyl, substituted cyclopropyl, cyclobutyl, substituted cyclobutyl, cyclopentyl, substituted cyclopentyl, cyclopropylmethyl, substituted cyclopropylmethyl, —$C_1$-$C_4$alkyl, and substituted —$C_1$-$C_4$alkyl;

$R^4R^{4'}$ are independently selected from: hydrogen, fluorine, cyclopropyl, substituted cyclopropyl, cyclobutyl, substituted cyclobutyl, cyclopentyl, substituted cyclopentyl, —$C_1$-$C_4$alkyl, and substituted —$C_1$-$C_4$alkyl,
or $R^4R^{4'}$ taken together with the carbon to which they are attached form cyclopropyl, substituted cyclopropyl, cyclobutyl, substituted cyclobutyl, cyclopentyl or substituted cyclopentyl;

$R^5R^{5'}$ are independently selected from: hydrogen, fluorine, cyclopropyl, substituted cyclopropyl, cyclobutyl, substituted cyclobutyl, cyclopentyl, substituted cyclopentyl, —$C_1$-$C_4$alkyl, and substituted —$C_1$-$C_4$alkyl, or $R^5R^{5'}$ taken together with the carbon to which they are attached form cyclopropyl, substituted cyclopropyl, cyclobutyl, substituted cyclobutyl, cyclopentyl or substituted cyclopentyl; and $R^1$ is selected from the group consisting of: hydrogen, —$C_1$-$C_4$alkyl and substituted —$C_1$-$C_4$alkyl; and when X is absent or $CR^{20}R^{21}$, $R^1$ can additionally be fluorine;

and/or pharmaceutically acceptable salts, hydrates, solvates and pro-drugs thereof.

This invention relates to a method of treating cancer, which comprises administering to a subject in need thereof an effective amount of an Akt/PKB inhibiting compound of Formula (I).

This invention relates to a method of treating arthritis, which comprises administering to a subject in need thereof an effective amount of an Akt/PKB inhibiting compound of Formula (I).

The present invention also relates to the discovery that the compounds of Formula (I) are active as inhibitors of Akt/PKB.

In a further aspect of the invention there is provided novel processes useful in preparing the presently invented Akt/PKB inhibiting compounds.

Included in the present invention are pharmaceutical compositions that comprise a pharmaceutical carrier and compounds useful in the methods of the invention.

Also included in the present invention are methods of co-administering the presently invented Akt/PKB inhibiting compounds with further active ingredients.

DETAILED DESCRIPTION OF THE INVENTION

International Application No. PCT/US2004/024340, having an International filing date of Jul. 28, 2004; International Publication Number WO 2005/011700 and an International Publication date of Feb. 10, 2005, the schemes, processes and assays of which are hereby incorporated by reference, discloses and claims 1H-imidazo[4,5-c]pyridin-2-yl containing compounds, along with pharmaceutically acceptable salts, hydrates, solvates and pro-drugs thereof, as being useful as inhibitors of serine/threonine kinase, Akt (also known as protein kinase B), particularly in the treatment of cancer and arthritis. International Application No. PCT/US2004/024340 does not specifically disclose any of the compounds within the scope of this application.

It has now been found that the compounds of Formula (I) exhibit advantages over what is considered to be the most structurally related compounds disclosed in International Application No. PCT/US2004/024340.

For example, the compounds of Examples 1, 3, 4 and 9 of the present invention generally exhibit enhanced activity and enhanced selectivity for the inhibition of tumor cell growth over inhibition of normal cell growth when compared to what is considered to be the most structurally related compounds disclosed in International Application No. PCT/US2004/024340. This enhanced activity and enhanced selectivity is expected to result in a wider therapeutic window. Additionally, the compounds disclosed in International Application No. PCT/US2004/024340 generally exhibit poor solubility in water. One aspect of this poor solubility is that it adversely affects the ability of these compounds to be formulated into pharmaceutical dosage forms suitable for intravenous (hereinafter IV) administration. In addition to generally having enhanced activity and enhanced selectivity for the inhibition of tumor cell growth over inhibition of normal cell growth, the compounds of Examples 1, 3, 4 and 9 of the present invention exhibit solubility that is considered suitable for formulation into dosage forms for IV administration. Intravenous administration is an advantageous method for administering the compounds of the present invention.

While the compounds of International Application No. PCT/US2004/024340 are useful as inhibitors of serine/threonine kinase, AKT (also known as protein kinase B), the compounds of Formula (I), particularly the compounds of Examples 1, 3, 4 and 9, generally exhibit advantageous properties, such as appropriate solubility, activity, selectivity, clearance and exposure, which overall render them advantageous over what is considered to be the most structurally related compounds disclosed in International Application No. PCT/US2004/024340.

This invention relates to compounds of Formula (I) as described above.

The presently invented compounds of Formula (I) inhibit Akt/PKB activity. In particular, the compounds disclosed herein inhibit each of the three Akt/PKB isoforms.

Included among the presently invented compounds of Formula (I) are those wherein:

X is absent or selected from the group consisting of: O, S and $CR^{20}R^{21}$, where $R^{20}R^{21}$ are independently selected from: hydrogen, fluorine, cyclopropyl, cyclobutyl, cyclopentyl, and —$C_1$-$C_4$alkyl, or $R^{20}R^{21}$ taken together with the carbon to which they are attached form cyclopropyl, cyclobutyl or cyclopentyl;

$R^2R^{2'}$ are independently selected from: hydrogen, fluorine, cyclopropyl, cyclobutyl, cyclopentyl, and —$C_1$-$C_4$alkyl, or $R^2R^{2'}$ taken together with the carbon to which they are attached form cyclopropyl, cyclobutyl or cyclopentyl;

$R^3$ is selected from the group consisting of: hydrogen, cyclopropyl, cyclobutyl, cyclopentyl, and —$C_1$-$C_4$alkyl;

$R^4R^{4'}$ are independently selected from: hydrogen, fluorine, cyclopropyl, cyclobutyl, cyclopentyl, and —$C_1$-$C_4$alkyl, or $R^4R^{4'}$ taken together with the carbon to which they are attached form cyclopropyl, cyclobutyl or cyclopentyl;

$R^5R^{5'}$ are independently selected from: hydrogen, fluorine, cyclopropyl, cyclobutyl, cyclopentyl, and —$C_1$-$C_4$alkyl, or $R^5R^{5'}$ taken together with the carbon to which they are attached form cyclopropyl, cyclobutyl or cyclopentyl; and $R^1$ is selected from the group consisting of: hydrogen and —$C_1$-$C_4$alkyl; and when X is absent or $CR^{20}R^{21}$, $R^1$ can additionally be fluorine;

and/or pharmaceutically acceptable salts, hydrates, solvates and pro-drugs thereof.

Included among the presently invented compounds of Formula (I) are those wherein:

X is absent or selected from the group consisting of: O, S and $CR^{20}R^{21}$, where $R^{20}R^{21}$ are independently selected from: hydrogen, fluorine, cyclopropyl, substituted cyclopropyl, cyclobutyl, substituted cyclobutyl, cyclopentyl, substituted cyclopentyl, —$C_1$-$C_4$alkyl, and substituted —$C_1$-$C_4$alkyl, or $R^{20}R^{21}$ taken together with the carbon to which they are attached form cyclopropyl, substituted cyclopropyl, cyclobutyl, substituted cyclobutyl, cyclopentyl or substituted cyclopentyl;

R²R²' are independently selected from: hydrogen, fluorine, cyclopropyl, substituted cyclopropyl, cyclobutyl, substituted cyclobutyl, cyclopentyl, substituted cyclopentyl, —$C_1$-$C_4$alkyl, and substituted —$C_1$-$C_4$alkyl,
    or R²R²' taken together with the carbon to which they are attached form cyclopropyl, substituted cyclopropyl, cyclobutyl, substituted cyclobutyl, cyclopentyl or substituted cyclopentyl;

R³ is selected from the group consisting of: hydrogen, cyclopropyl, substituted cyclopropyl, cyclobutyl, substituted cyclobutyl, cyclopentyl, substituted cyclopentyl, —$C_1$-$C_4$alkyl and substituted —$C_1$-$C_4$alkyl;

R⁴R⁴' are independently selected from: hydrogen, fluorine, cyclopropyl, substituted cyclopropyl, cyclobutyl, substituted cyclobutyl, cyclopentyl, substituted cyclopentyl, —$C_1$-$C_4$alkyl, and substituted —$C_1$-$C_4$alkyl,
    or R⁴R⁴' taken together with the carbon to which they are attached form cyclopropyl, substituted cyclopropyl, cyclobutyl, substituted cyclobutyl, cyclopentyl or substituted cyclopentyl;

R⁵R⁵' are independently selected from: hydrogen, fluorine, cyclopropyl, substituted cyclopropyl, cyclobutyl, substituted cyclobutyl, cyclopentyl, substituted cyclopentyl, —$C_1$-$C_4$alkyl, and substituted —$C_1$-$C_4$alkyl,
    or R⁵R⁵' taken together with the carbon to which they are attached form cyclopropyl, substituted cyclopropyl, cyclobutyl, substituted cyclobutyl, cyclopentyl or substituted cyclopentyl; and R¹ is selected from the group consisting of: hydrogen, —$C_1$-$C_4$alkyl and substituted —$C_1$-$C_4$alkyl; and
when X is absent or CR²⁰R²¹, R¹ can additionally be fluorine;

and/or pharmaceutically acceptable salts, hydrates, solvates and pro-drugs thereof.

Included among the presently invented compounds of Formula (I) are those wherein:

X is absent or selected from the group consisting of: O, S and CR²⁰R²¹, where R²⁰R²¹ are independently selected from: hydrogen, fluorine, cyclopropyl, cyclobutyl, cyclopentyl, and —$C_1$-$C_4$alkyl;

R²R²' are independently selected from: hydrogen, fluorine, cyclopropyl, cyclobutyl, cyclopentyl, and —$C_1$-$C_4$alkyl;

R³ is selected from the group consisting of: hydrogen, cyclopropyl, cyclobutyl, cyclopentyl, and —$C_1$-$C_4$alkyl;

R⁴R⁴' are independently selected from: hydrogen, fluorine, cyclopropyl, cyclobutyl, cyclopentyl, and —$C_1$-$C_4$alkyl;

R⁵R⁵' are independently selected from: hydrogen, fluorine, cyclopropyl, cyclobutyl, cyclopentyl, and —$C_1$-$C_4$alkyl; and R¹ is selected from the group consisting of: hydrogen and —$C_1$-$C_4$alkyl; and
when X is absent or CR²⁰R²¹, R¹ can additionally be fluorine;

and/or pharmaceutically acceptable salts, hydrates, solvates and pro-drugs thereof.

Included among the presently invented compounds of Formula (I) are those wherein:

X is absent or selected from the group consisting of: O, S and CR²⁰R²¹, where R²⁰R²¹ are independently selected from: hydrogen, fluorine, cyclopropyl, substituted cyclopropyl, cyclobutyl, substituted cyclobutyl, cyclopentyl, substituted cyclopentyl, —$C_1$-$C_4$alkyl and substituted —$C_1$-$C_4$alkyl;

R²R²' are independently selected from: hydrogen, fluorine, cyclopropyl, substituted cyclopropyl, cyclobutyl, substituted cyclobutyl, cyclopentyl, substituted cyclopentyl, —$C_1$-$C_4$alkyl and substituted —$C_1$-$C_4$alkyl;

R³ is selected from the group consisting of: hydrogen, cyclopropyl, substituted cyclopropyl, cyclobutyl, substituted cyclobutyl, cyclopentyl, substituted cyclopentyl, —$C_1$-$C_4$alkyl and substituted —$C_1$-$C_4$alkyl;

R⁴R⁴' are independently selected from: hydrogen, fluorine, cyclopropyl, substituted cyclopropyl, cyclobutyl, substituted cyclobutyl, cyclopentyl, substituted cyclopentyl, —$C_1$-$C_4$alkyl and substituted —$C_1$-$C_4$alkyl;

R⁵R⁵' are independently selected from: hydrogen, fluorine, cyclopropyl, substituted cyclopropyl, cyclobutyl, substituted cyclobutyl, cyclopentyl, substituted cyclopentyl, —$C_1$-$C_4$alkyl and substituted —$C_1$-$C_4$alkyl; and R¹ is selected from the group consisting of: hydrogen, —$C_1$-$C_4$alkyl and substituted —$C_1$-$C_4$alkyl; and
when X is absent or CR²⁰R²¹, R¹ can additionally be fluorine;

and/or pharmaceutically acceptable salts, hydrates, solvates and pro-drugs thereof.

Included among the presently invented compounds of Formula (I) are:

4-(2-(4-amino-1,2,5-oxadiazol-3-yl)-1-ethyl-7-{[(3S)-3-piperidinylmethyl]oxy}-1H-imidazo[4,5-c]pyridin-4-yl)-2-methyl-3-butyn-2-ol;

4-{2-(4-amino-1,2,5-oxadiazol-3-yl)-1-ethyl-7-[(2-morpholinylmethyl)oxy]-1H-imidazo[4,5-c]pyridin-4-yl}-2-methyl-3-butyn-2-ol;

4-(2-(4-amino-1,2,5-oxadiazol-3-yl)-1-ethyl-7-{[(2S)-2-thiomorpholinylmethyl]oxy}-1H-imidazo[4,5-c]pyridin-4-yl)-2-methyl-3-butyn-2-ol;

4-(2-(4-amino-1,2,5-oxadiazol-3-yl)-1-ethyl-7-{[(2S)-2-morpholinylmethyl]oxy}-1H-imidazo[4,5-c]pyridin-4-yl)-2-methyl-3-butyn-2-ol;

4-{2-(4-amino-1,2,5-oxadiazol-3-yl)-1-ethyl-7-[(3-pyrrolidinylmethyl)oxy]-1H-imidazo[4,5-c]pyridin-4-yl}-2-methyl-3-butyn-2-ol;

4-[2-(4-amino-1,2,5-oxadiazol-3-yl)-1-ethyl-7-({[(3S)-1-methyl-3-piperidinyl]methyl}oxy)-1H-imidazo[4,5-c]pyridin-4-yl]-2-methyl-3-butyn-2-ol;

4-[2-(4-amino-1,2,5-oxadiazol-3-yl)-1-ethyl-7-({[(2S)-4-methyl-2-thiomorpholinyl]methyl}oxy)-1H-imidazo[4,5-c]pyridin-4-yl]-2-methyl-3-butyn-2-ol;

4-[2-(4-amino-1,2,5-oxadiazol-3-yl)-1-ethyl-7-({[(2S)-4-methyl-2-morpholinyl]methyl}oxy)-1H-imidazo[4,5-c]pyridin-4-yl]-2-methyl-3-butyn-2-ol;

4-[2-(4-amino-1,2,5-oxadiazol-3-yl)-1-ethyl-7-({[(2R)-6-methyl-2-morpholinyl]methyl}oxy)-1H-imidazo[4,5-c]pyridin-4-yl]-2-methyl-3-butyn-2-ol; and 4-[2-(4-amino-1,2,5-oxadiazol-3-yl)-1-ethyl-7-({[(2S)-4-ethyl-2-morpholinyl]methyl}oxy)-1H-imidazo[4,5-c]pyridin-4-yl]-2-methyl-3-butyn-2-ol;

and/or pharmaceutically acceptable salts, hydrates, solvates and pro-drugs thereof.

Compounds of Formula (I) are included in the pharmaceutical compositions of the invention and used in the methods of the invention.

As used herein, the substituents cyclopropyl, cyclopropylmethyl, cyclobutyl, cyclopentyl and —$C_1$-$C_4$alkyl, are optionally substituted with from 1 fluorine atom to where the substituent is perfluorinated. Suitably, the substituent is optionally substituted with from 1 to 8 fluorine atoms. Suitably, the substituent is optionally substituted with from 1 to 5 fluorine atoms. Suitably, the substituent is optionally substituted with from 1 to 3 fluorine atoms.

By the term "perfluorinated" as used herein is meant a substituent where all of the hydrogen atoms have been replaced by fluorine atoms.

By the term "substituted" as used herein, unless otherwise defined, is meant that the subject chemical moiety is substituted with from 1 fluorine atom to where the chemical moiety is perfluorinated. Suitably, the chemical moiety is substituted with from 1 to 8 fluorine atoms. Suitably, the chemical moiety is substituted with from 1 to 5 fluorine atoms. Suitably, the chemical moiety is substituted with from 1 to 3 fluorine atoms.

By the term "—$C_1$-$C_4$alkyl" as used herein, is meant a linear or branched, saturated or unsaturated hydrocarbon chain, containing from 1 to 4 carbon atoms. Examples of —$C_1$-$C_4$alkyl as used herein include: —$CH_3$, —$CH_2$—$CH_3$, —$CH_2$—$CH_2$—$CH_3$, —$CH(CH_3)_2$, —$CH_2$—$CF_3$, —$C(CH_3)_3$, —$(CH_2)_3$—$CH_3$, —$CH_2$—$CH(CH_3)_2$, —$CH(CH_3)$—$CH_2$—$CH_3$, —$CH$=$CH_2$, and —$C$≡$C$—$CH_3$.

Unless otherwise stated, the compounds disclosed herein also include all stereochemical forms of the structure; i.e., the R and S configurations for each asymmetric center. Therefore, single stereochemical isomers as well as enantiomeric and diastereomeric mixtures of the present compounds are within the scope of the invention.

By the term "treating" and derivatives thereof as used herein, is meant prophylatic and therapeutic therapy.

As used herein, the term "effective amount" and derivatives thereof means that amount of a drug or pharmaceutical agent that will elicit the biological or medical response of a tissue, system, animal or human that is being sought, for instance, by a researcher or clinician. Furthermore, the term "therapeutically effective amount" and derivatives thereof means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

The novel compounds of Formula I are prepared as shown in Scheme 1 below, or by analogous methods. All of the starting materials are commercially available or are readily made from commercially available starting materials by those of skill in the art.

Scheme 1

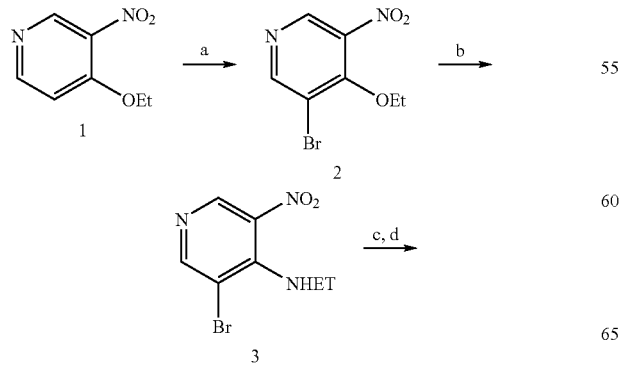

-continued

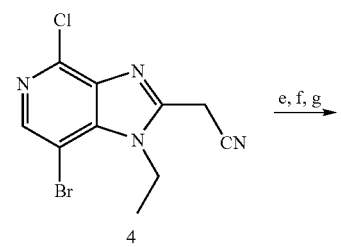

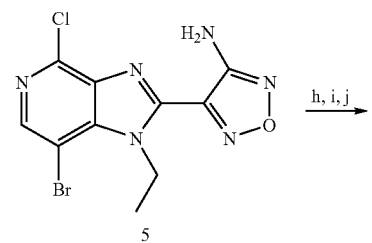

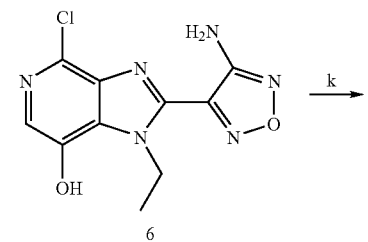

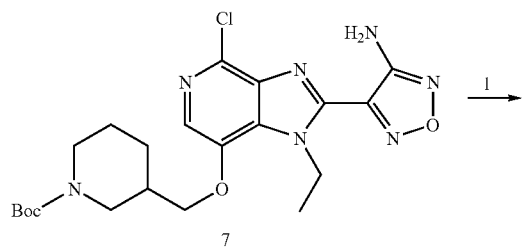

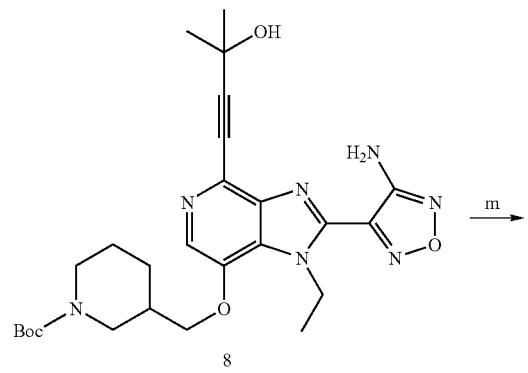

-continued

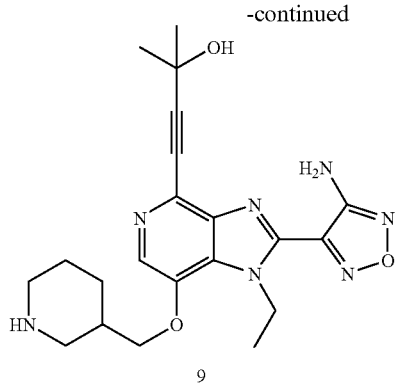

9

(a) Br₂, NaOAc; (b) EtNH₂; (c) SnCl₂, HCl; (d) ethyl cyanoacetate, 190° C.;
(e) NaNO₂, HCl; (f) NH₂OH; (g) Et₃N, dioxane; (h) n-BuLi, THF; (i) B(OMe)₃;
(j) H₂O₂, NaOH; (k) 1,1-dimethylethyl 3-(hydroxymethyl)-1-piperidinecarboxylate,
DEAD, polymer bound PPh₃, CH₂Cl₂; (l) Pd(PPh₃)₄, iPr₂NH, dioxane, 100° C.;
(m) TFA, CH₂Cl₂.

Compounds of Formula (I) can be prepared in a manner analogous to those shown in Scheme 1. Bromination of 3-nitro-4-ethoxy pyridine (1-Scheme 1) using bromine buffered in sodium acetate gives 3-bromo-4-(ethyloxy)-5-nitropyridine (2-Scheme 1). Other alternative methods exist and are known to those skilled in the art for carrying out this transformation. A compilation of these methods can be found in standard organic synthesis texts such as Larock, "Comprehensive Organic Transformations," VCH, N.Y. (1989). The ethoxy group is then displaced by a primary amine such as ethyl amine in a polar solvent such as ethanol to give compounds such as 3-Scheme 1. In the case liquid amines, the reaction can be carried out in the absence of solvent. The reduction of the nitro group with concomitant introduction of the chloro group is achieved using tin (II) chloride according to the method described by Kelley et al. J. Med. Chem. 1995, 38(20), 4131-34. The corresponding 5-bromo-2-chloro diaminopyridine is condensed with an appropriate acid or ester such as ethyl cyanoacetate. Continued heating affects a cyclodehydration reaction to give imidazopyridines such as 4-Scheme 1. Reaction with NaNO₂ in concentrated HCl following by reaction with hydroxylamine gives a bis-oxime that cyclodehydrates in the presence of an appropriate base such as triethylamine to give an aminofurazan such as 5-Scheme 1. The hydroxyl group is introduced by generating an aryl anion by halogen-metal exchange using a suitable base such as n-butyl lithium, reacting the anion with an appropriate boron electrophile such as trimethyl borate and oxidizing the resulting aryl boronate with an appropriate oxidizing agent such as hydrogen peroxide in aqueous base to give imidazopyridinols such as 6-Scheme 1. Other bases such as Grignard reagents can also be used to affect the halogen metal exchange. Etherification of the imidazopyridinol is carried out with an appropriate alcohol such as 1,1-dimethylethyl 3-(hydroxymethyl)-1-piperidinecarboxylate using the methods described by Mitsunobu, Synthesis 1981, 1 to give ethers such as 7-Scheme 1. Alternatively, the etherification can be carried out by reacting an appropriate halide such as 1,1-dimethylethyl 3-(chloromethyl)-1-piperidinecarboxylate with a suitable alcohol such as 6-Scheme 1 in the presence of a suitable base such as potassium carbonate. Treatment of an appropriate aryl halide such as 7-Scheme 1 with an appropriate catalyst such as tetrakistriphenylphosphine palladium and a terminal alkyne in the presence of a suitable base such as di-isopropylamine in an appropriate solvent such as dioxane gives the corresponding aryl alkyne such as 8-Scheme 1. Removal of the protecting groups is achieved using a protic or Lewis acid such as trifluoroacetic acid in a polar solvent such as methylene chloride giving compounds of Formula (I) such as 9-Scheme 1.

By the term "co-administering" and derivatives thereof as used herein is meant either simultaneous administration or any manner of separate sequential administration of an AKT inhibiting compound, as described herein, and a further active ingredient or ingredients, known to be useful in the treatment of cancer, including chemotherapy and radiation treatment, or to be useful in the treatment of arthritis. The term further active ingredient or ingredients, as used herein, includes any compound or therapeutic agent known to or that demonstrates advantageous properties when administered to a patient in need of treatment for cancer or arthritis. Preferably, if the administration is not simultaneous, the compounds are administered in a close time proximity to each other. Furthermore, it does not matter if the compounds are administered in the same dosage form, e.g. one compound may be administered topically and another compound may be administered orally.

Typically, any anti-neoplastic agent that has activity versus a susceptible tumor being treated may be co-administered in the treatment of cancer in the present invention. Examples of such agents can be found in Cancer Principles and Practice of Oncology by V. T. Devita and S. Hellman (editors), 6$^{th}$ edition (Feb. 15, 2001), Lippincott Williams & Wilkins Publishers. A person of ordinary skill in the art would be able to discern which combinations of agents would be useful based on the particular characteristics of the drugs and the cancer involved. Typical anti-neoplastic agents useful in the present invention include, but are not limited to, anti-microtubule agents such as diterpenoids and vinca alkaloids; platinum coordination complexes; alkylating agents such as nitrogen mustards, oxazaphosphorines, alkylsulfonates, nitrosoureas, and triazenes; antibiotic agents such as anthracyclines, actinomycins and bleomycins; topoisomerase II inhibitors such as epipodophyllotoxins; antimetabolites such as purine and pyrimidine analogues and anti-folate compounds; topoisomerase I inhibitors such as camptothecins; hormones and hormonal analogues; signal transduction pathway inhibitors; non-receptor tyrosine kinase angiogenesis inhibitors; immunotherapeutic agents; proapoptotic agents; and cell cycle signaling inhibitors.

Examples of a further active ingredient or ingredients (anti-neoplastic agent) for use in combination or co-administered with the presently invented AKT inhibiting compounds are chemotherapeutic agents.

Anti-microtubule or anti-mitotic agents are phase specific agents active against the microtubules of tumor cells during M or the mitosis phase of the cell cycle. Examples of anti-microtubule agents include, but are not limited to, diterpenoids and vinca alkaloids.

Diterpenoids, which are derived from natural sources, are phase specific anti-cancer agents that operate at the G₂/M phases of the cell cycle. It is believed that the diterpenoids stabilize the β-tubulin subunit of the microtubules, by binding with this protein. Disassembly of the protein appears then to be inhibited with mitosis being arrested and cell death following. Examples of diterpenoids include, but are not limited to, paclitaxel and its analog docetaxel.

Paclitaxel, 5β,20-epoxy-1,2α,4,7β,10β,13α-hexa-hydroxytax-11-en-9-one 4,10-diacetate 2-benzoate 13-ester with (2R,3S)—N-benzoyl-3-phenylisoserine; is a natural diterpene product isolated from the Pacific yew tree *Taxus brevifolia* and is commercially available as an injectable solution TAXOL®. It is a member of the taxane family of terpenes. It was first isolated in 1971 by Wani et al. J. Am. Chem., Soc., 93:2325. 1971), who characterized its structure by chemical and X-ray crystallographic methods. One mechanism for its activity relates to paclitaxel's capacity to bind tubulin, thereby inhibiting cancer cell growth. Schiff et al., Proc. Natl, Acad, Sci. USA, 77:1561-1565 (1980); Schiff et al., Nature, 277:665-667 (1979); Kumar, J. Biol, Chem, 256: 10435-10441 (1981). For a review of synthesis and anticancer activity of some paclitaxel derivatives see: D. G. I. Kingston et al., Studies in Organic Chemistry vol. 26, entitled "New trends in Natural Products Chemistry 1986", Attaur-Rahman, P. W. Le Quesne, Eds. (Elsevier, Amsterdam, 1986) pp 219-235.

Paclitaxel has been approved for clinical use in the treatment of refractory ovarian cancer in the United States (Markman et al., Yale Journal of Biology and Medicine, 64:583, 1991; McGuire et al., Ann. Intem, Med., 111:273, 1989) and for the treatment of breast cancer (Holmes et al., J. Nat. Cancer Inst., 83:1797, 1991.) It is a potential candidate for treatment of neoplasms in the skin (Einzig et. al., Proc. Am. Soc. Clin. Oncol., 20:46) and head and neck carcinomas (Forastire et. al., Sem. Oncol., 20:56, 1990). The compound also shows potential for the treatment of polycystic kidney disease (Woo et. al., Nature, 368:750. 1994), lung cancer and malaria. Treatment of patients with paclitaxel results in bone marrow suppression (multiple cell lineages, Ignoff, R. J. et. al, Cancer Chemotherapy Pocket Guide, 1998) related to the duration of dosing above a threshold concentration (50 nM) (Kearns, C. M. et. al., Seminars in Oncology, 3(6) p. 16-23, 1995).

Docetaxel, (2R,3S)—N-carboxy-3-phenylisoserine, N-tert-butyl ester, 13-ester with 5β-20-epoxy-1,2α,4,7β,10β,13α-hexahydroxytax-11-en-9-one 4-acetate 2-benzoate, trihydrate; is commercially available as an injectable solution as TAXOTERE®. Docetaxel is indicated for the treatment of breast cancer. Docetaxel is a semisynthetic derivative of paclitaxel q.v., prepared using a natural precursor, 10-deacetyl-baccatin III, extracted from the needle of the European Yew tree. The dose limiting toxicity of docetaxel is neutropenia.

Vinca alkaloids are phase specific anti-neoplastic agents derived from the periwinkle plant. Vinca alkaloids act at the M phase (mitosis) of the cell cycle by binding specifically to tubulin. Consequently, the bound tubulin molecule is unable to polymerize into microtubules. Mitosis is believed to be arrested in metaphase with cell death following. Examples of vinca alkaloids include, but are not limited to, vinblastine, vincristine, and vinorelbine.

Vinblastine, vincaleukoblastine sulfate, is commercially available as VELBAN® as an injectable solution. Although, it has possible indication as a second line therapy of various solid tumors, it is primarily indicated in the treatment of testicular cancer and various lymphomas including Hodgkin's Disease; and lymphocytic and histiocytic lymphomas. Myelosuppression is the dose limiting side effect of vinblastine.

Vincristine, vincaleukoblastine, 22-oxo-, sulfate, is commercially available as ONCOVIN® as an injectable solution. Vincristine is indicated for the treatment of acute leukemias and has also found use in treatment regimens for Hodgkin's and non-Hodgkin's malignant lymphomas. Alopecia and neurologic effects are the most common side effect of vincristine and to a lesser extent myelosupression and gastrointestinal mucositis effects occur.

Vinorelbine, 3',4'-didehydro-4'-deoxy-C'-norvincaleukoblastine[R—(R*,R*)-2,3-dihydroxybutanedioate (1:2) (salt)], commercially available as an injectable solution of vinorelbine tartrate (NAVELBINE®), is a semisynthetic vinca alkaloid. Vinorelbine is indicated as a single agent or in combination with other chemotherapeutic agents, such as cisplatin, in the treatment of various solid tumors, particularly non-small cell lung, advanced breast, and hormone refractory prostate cancers. Myelosuppression is the most common dose limiting side effect of vinorelbine.

Platinum coordination complexes are non-phase specific anti-cancer agents, which are interactive with DNA. The platinum complexes enter tumor cells, undergo, aquation and form intra- and interstrand crosslinks with DNA causing adverse biological effects to the tumor. Examples of platinum coordination complexes include, but are not limited to, cisplatin and carboplatin.

Cisplatin, cis-diamminedichloroplatinum, is commercially available as PLATINOL® as an injectable solution. Cisplatin is primarily indicated in the treatment of metastatic testicular and ovarian cancer and advanced bladder cancer. The primary dose limiting side effects of cisplatin are nephrotoxicity, which may be controlled by hydration and diuresis, and ototoxicity.

Carboplatin, platinum, diammine[1,1-cyclobutane-dicarboxylate(2-)-O,O'], is commercially available as PARAPLATIN® as an injectable solution. Carboplatin is primarily indicated in the first and second line treatment of advanced ovarian carcinoma. Bone marrow suppression is the dose limiting toxicity of carboplatin.

Alkylating agents are non-phase anti-cancer specific agents and strong electrophiles. Typically, alkylating agents form covalent linkages, by alkylation, to DNA through nucleophilic moieties of the DNA molecule such as phosphate, amino, sulfhydryl, hydroxyl, carboxyl, and imidazole groups. Such alkylation disrupts nucleic acid function leading to cell death. Examples of alkylating agents include, but are not limited to, nitrogen mustards such as cyclophosphamide, melphalan, and chlorambucil; alkyl sulfonates such as busulfan; nitrosoureas such as carmustine; and triazenes such as dacarbazine.

Cyclophosphamide, 2-[bis(2-chloroethyl)amino]tetrahydro-2H-1,3,2-oxazaphosphorine 2-oxide monohydrate, is commercially available as an injectable solution or tablets as CYTOXAN®. Cyclophosphamide is indicated as a single agent or in combination with other chemotherapeutic agents, in the treatment of malignant lymphomas, multiple myeloma, and leukemias. Alopecia, nausea, vomiting and leukopenia are the most common dose limiting side effects of cyclophosphamide.

Melphalan, 4-[bis(2-chloroethyl)amino]-L-phenylalanine, is commercially available as an injectable solution or tablets as ALKERAN®. Melphalan is indicated for the palliative treatment of multiple myeloma and non-respectable epithelial carcinoma of the ovary. Bone marrow suppression is the most common dose limiting side effect of melphalan.

Chlorambucil, 4-[bis(2-chloroethyl)amino]benzenebutanoic acid, is commercially available as LEUKERAN® tablets. Chlorambucil is indicated for the palliative treatment of chronic lymphatic leukemia, and malignant lymphomas such as lymphosarcoma, giant follicular lymphoma, and Hodgkin's disease. Bone marrow suppression is the most common dose limiting side effect of chlorambucil.

Busulfan, 1,4-butanediol dimethanesulfonate, is commercially available as MYLERAN® TABLETS. Busulfan is indicated for the palliative treatment of chronic myelogenous leukemia. Bone marrow suppression is the most common dose limiting side effects of busulfan.

Carmustine, 1,3-[bis(2-chloroethyl)-1-nitrosourea, is commercially available as single vials of lyophilized material as BiCNU®. Carmustine is indicated for the palliative treatment as a single agent or in combination with other agents for brain tumors, multiple myeloma, Hodgkin's disease, and non-Hodgkin's lymphomas. Delayed myelosuppression is the most common dose limiting side effects of carmustine.

Dacarbazine, 5-(3,3-dimethyl-1-triazeno)-imidazole-4-carboxamide, is commercially available as single vials of material as DTIC-Dome®. Dacarbazine is indicated for the treatment of metastatic malignant melanoma and in combination with other agents for the second line treatment of Hodgkin's Disease. Nausea, vomiting, and anorexia are the most common dose limiting side effects of dacarbazine.

Antibiotic anti-neoplastics are non-phase specific agents, which bind or intercalate with DNA. Typically, such action results in stable DNA complexes or strand breakage, which disrupts ordinary function of the nucleic acids leading to cell death. Examples of antibiotic anti-neoplastic agents include, but are not limited to, actinomycins such as dactinomycin, anthrocyclins such as daunorubicin and doxorubicin; and bleomycins.

Dactinomycin, also know as Actinomycin D, is commercially available in injectable form as COSMEGEN®. Dactinomycin is indicated for the treatment of Wilm's tumor and rhabdomyosarcoma. Nausea, vomiting, and anorexia are the most common dose limiting side effects of dactinomycin.

Daunorubicin, (8S-cis-)-8-acetyl-10-[(3-amino-2,3,6-trideoxy-α-L-lyxo-hexopyranosyl)oxy]-7,8,9,10-tetrahydro-6,8,11-trihydroxy-1-methoxy-5,12 naphthacenedione hydrochloride, is commercially available as a liposomal injectable form as DAUNOXOME® or as an injectable as CERUBIDINE®. Daunorubicin is indicated for remission induction in the treatment of acute nonlymphocytic leukemia and advanced HIV associated Kaposi's sarcoma. Myelosuppression is the most common dose limiting side effect of daunorubicin.

Doxorubicin, (8S,10S)-10-[(3-amino-2,3,6-trideoxy-α-L-lyxo-hexopyranosyl)oxy]-8-glycoloyl, 7,8,9,10-tetrahydro-6,8,11-trihydroxy-1-methoxy-5,12-naphthacenedione hydrochloride, is commercially available as an injectable form as RUBEX® or ADRIAMYCIN RDF®. Doxorubicin is primarily indicated for the treatment of acute lymphoblastic leukemia and acute myeloblastic leukemia, but is also a useful component in the treatment of some solid tumors and lymphomas. Myelosuppression is the most common dose limiting side effect of doxorubicin.

Bleomycin, a mixture of cytotoxic glycopeptide antibiotics isolated from a strain of *Streptomyces verticillus*, is commercially available as BLENOXANE®. Bleomycin is indicated as a palliative treatment, as a single agent or in combination with other agents, of squamous cell carcinoma, lymphomas, and testicular carcinomas. Pulmonary and cutaneous toxicities are the most common dose limiting side effects of bleomycin.

Topoisomerase II inhibitors include, but are not limited to, epipodophyllotoxins.

Epipodophyllotoxins are phase specific anti-neoplastic agents derived from the mandrake plant. Epipodophyllotoxins typically affect cells in the S and $G_2$ phases of the cell cycle by forming a ternary complex with topoisomerase II and DNA causing DNA strand breaks. The strand breaks accumulate and cell death follows. Examples of epipodophyllotoxins include, but are not limited to, etoposide and teniposide.

Etoposide, 4'-demethyl-epipodophyllotoxin 9[4,6-0-(R)-ethylidene-β-D-glucopyranoside], is commercially available as an injectable solution or capsules as VePESID® and is commonly known as VP-16. Etoposide is indicated as a single agent or in combination with other chemotherapy agents in the treatment of testicular and non-small cell lung cancers. Myelosuppression is the most common side effect of etoposide. The incidence of leukopenia tends to be more severe than thrombocytopenia.

Teniposide, 4'-demethyl-epipodophyllotoxin 9[4,6-0-(R)-thenylidene-β-D-glucopyranoside], is commercially available as an injectable solution as VUMON® and is commonly known as VM-26. Teniposide is indicated as a single agent or in combination with other chemotherapy agents in the treatment of acute leukemia in children. Myelosuppression is the most common dose limiting side effect of teniposide. Teniposide can induce both leukopenia and thrombocytopenia.

Antimetabolite neoplastic agents are phase specific antineoplastic agents that act at S phase (DNA synthesis) of the cell cycle by inhibiting DNA synthesis or by inhibiting purine or pyrimidine base synthesis and thereby limiting DNA synthesis. Consequently, S phase does not proceed and cell death follows. Examples of antimetabolite anti-neoplastic agents include, but are not limited to, fluorouracil, methotrexate, cytarabine, mercaptopurine, thioguanine, and gemcitabine.

5-fluorouracil, 5-fluoro-2,4-(1H,3H) pyrimidinedione, is commercially available as fluorouracil. Administration of 5-fluorouracil leads to inhibition of thymidylate synthesis and is also incorporated into both RNA and DNA. The result typically is cell death. 5-fluorouracil is indicated as a single agent or in combination with other chemotherapy agents in the treatment of carcinomas of the breast, colon, rectum, stomach and pancreas. Myelosuppression and mucositis are dose limiting side effects of 5-fluorouracil. Other fluoropyrimidine analogs include 5-fluoro deoxyuridine (floxuridine) and 5-fluorodeoxyuridine monophosphate.

Cytarabine, 4-amino-1-β-D-arabinofuranosyl-2(1H)-pyrimidinone, is commercially available as CYTOSAR-U® and is commonly known as Ara-C. It is believed that cytarabine exhibits cell phase specificity at S-phase by inhibiting DNA chain elongation by terminal incorporation of cytarabine into the growing DNA chain. Cytarabine is indicated as a single agent or in combination with other chemotherapy agents in the treatment of acute leukemia. Other cytidine analogs include 5-azacytidine and 2',2'-difluorodeoxycytidine (gemcitabine). Cytarabine induces leukopenia, thrombocytopenia, and mucositis.

Mercaptopurine, 1,7-dihydro-6H-purine-6-thione monohydrate, is commercially available as PURINETHOL®. Mercaptopurine exhibits cell phase specificity at S-phase by inhibiting DNA synthesis by an as of yet unspecified mechanism. Mercaptopurine is indicated as a single agent or in combination with other chemotherapy agents in the treatment of acute leukemia. Myelosuppression and gastrointestinal mucositis are expected side effects of mercaptopurine at high doses. A useful mercaptopurine analog is azathioprine.

Thioguanine, 2-amino-1,7-dihydro-6H-purine-6-thione, is commercially available as TABLOID®. Thioguanine exhibits cell phase specificity at S-phase by inhibiting DNA synthesis by an as of yet unspecified mechanism. Thioguanine is indicated as a single agent or in combination with other chemotherapy agents in the treatment of acute leukemia. Myelosuppression, including leukopenia, thrombocytopenia, and anemia, is the most common dose limiting side effect of thioguanine administration. However, gastrointestinal side effects occur and can be dose limiting. Other purine analogs include pentostatin, erythrohydroxynonyladenine, fludarabine phosphate, and cladribine.

Gemcitabine, 2'-deoxy-2',2'-difluorocytidine monohydrochloride (β-isomer), is commercially available as GEMZAR®. Gemcitabine exhibits cell phase specificity at S-phase and by blocking progression of cells through the G1/S boundary. Gemcitabine is indicated in combination with cisplatin in the treatment of locally advanced non-small cell lung cancer and alone in the treatment of locally advanced pancreatic cancer. Myelosuppression, including leukopenia, thrombocytopenia, and anemia, is the most common dose limiting side effect of gemcitabine administration.

Methotrexate, N-[4[[(2,4-diamino-6-pteridinyl)methyl]methylamino]benzoyl]-L-glutamic acid, is commercially available as methotrexate sodium. Methotrexate exhibits cell phase effects specifically at S-phase by inhibiting DNA synthesis, repair and/or replication through the inhibition of dyhydrofolic acid reductase which is required for synthesis of purine nucleotides and thymidylate. Methotrexate is indicated as a single agent or in combination with other chemotherapy agents in the treatment of choriocarcinoma, meningeal leukemia, non-Hodgkin's lymphoma, and carcinomas of the breast, head, neck, ovary and bladder. Myelosuppression (leukopenia, thrombocytopenia, and anemia) and mucositis are expected side effect of methotrexate administration.

Camptothecins, including, camptothecin and camptothecin derivatives are available or under development as Topoisomerase I inhibitors. Camptothecins cytotoxic activity is believed to be related to its Topoisomerase I inhibitory activity. Examples of camptothecins include, but are not limited to irinotecan, topotecan, and the various optical forms of 7-(4-methylpiperazino-methylene)-10,11-ethylenedioxy-20-camptothecin described below.

Irinotecan HCl, (4S)-4,11-diethyl-4-hydroxy-9-[(4-piperidinopiperidino) carbonyloxy]-1H-pyrano[3',4',6,7]indolizino[1,2-b]quinoline-3,14-(4H, 12H)-dione hydrochloride, is commercially available as the injectable solution CAMPTOSAR®.

Irinotecan is a derivative of camptothecin which binds, along with its active metabolite SN-38, to the topoisomerase I-DNA complex. It is believed that cytotoxicity occurs as a result of irreparable double strand breaks caused by interaction of the topoisomerase I:DNA:irintecan or SN-38 ternary complex with replication enzymes. Irinotecan is indicated for treatment of metastatic cancer of the colon or rectum. The dose limiting side effects of irinotecan HCl are myelosuppression, including neutropenia, and GI effects, including diarrhea.

Topotecan HCl, (S)-10-[(dimethylamino)methyl]-4-ethyl-4,9-dihydroxy-1H-pyrano[3',4',6,7]indolizino[1,2-b]quinoline-3,14-(4H,12H)-dione monohydrochloride, is commercially available as the injectable solution HYCAMTIN®. Topotecan is a derivative of camptothecin which binds to the topoisomerase I-DNA complex and prevents relegation of singles strand breaks caused by Topoisomerase I in response to torsional strain of the DNA molecule. Topotecan is indicated for second line treatment of metastatic carcinoma of the ovary and small cell lung cancer. The dose limiting side effect of topotecan HCl is myelosuppression, primarily neutropenia.

Also of interest, is the camptothecin derivative of formula A following, currently under development, including the racemic mixture (R,S) form as well as the R and S enantiomers:

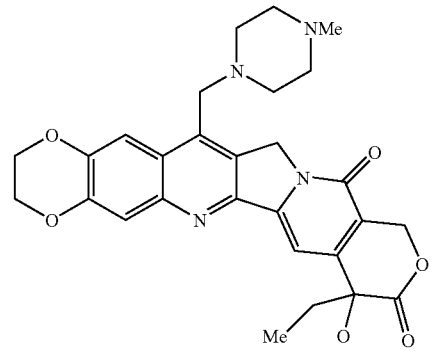

A known by the chemical name "7-(4-methylpiperazino-methylene)-10,11-ethylenedioxy-20-(R,S)-camptothecin (racemic mixture) or "7-(4-methylpiperazinomethylene)-10,11-ethylenedioxy-20-(R)-camptothecin (R enantiomer) or "7-(4-methylpiperazino-methylene)-10,11-ethylenedioxy-20-(S)-camptothecin (S enantiomer). Such compound as well as related compounds are described, including methods of making, in U.S. Pat. Nos. 6,063,923; 5,342,947; 5,559,235; 5,491,237 and pending U.S. patent application Ser. No. 08/977,217 filed Nov. 24, 1997.

Hormones and hormonal analogues are useful compounds for treating cancers in which there is a relationship between the hormone(s) and growth and/or lack of growth of the cancer. Examples of hormones and hormonal analogues useful in cancer treatment include, but are not limited to, adrenocorticosteroids such as prednisone and prednisolone which are useful in the treatment of malignant lymphoma and acute leukemia in children; aminoglutethimide and other aromatase inhibitors such as anastrozole, letrazole, vorazole, and exemestane useful in the treatment of adrenocortical carcinoma and hormone dependent breast carcinoma containing estrogen receptors; progestins such as megestrol acetate useful in the treatment of hormone dependent breast cancer and endometrial carcinoma; estrogens, androgens, and anti-androgens such as flutamide, nilutamide, bicalutamide, cyproterone acetate and 5α-reductases such as finasteride and dutasteride, useful in the treatment of prostatic carcinoma and benign prostatic hypertrophy; anti-estrogens such as tamoxifen, toremifene, raloxifene, droloxifene, iodoxyfene, as well as selective estrogen receptor modulators (SERMS) such those described in U.S. Pat. Nos. 5,681,835, 5,877,219, and 6,207,716, useful in the treatment of hormone dependent breast carcinoma and other susceptible cancers; and gonadotropin-releasing hormone (GnRH) and analogues thereof which stimulate the release of leutinizing hormone (LH) and/or follicle stimulating hormone (FSH) for the treatment prostatic carcinoma, for instance, LHRH agonists and antagonists such as goserelin acetate and luprolide.

Signal transduction pathway inhibitors are those inhibitors, which block or inhibit a chemical process which evokes an intracellular change. As used herein this change is cell proliferation or differentiation. Signal transduction inhibitors useful in the present invention include inhibitors of receptor tyrosine kinases, non-receptor tyrosine kinases, SH2/SH3 domain blockers, serine/threonine kinases, phosphotidyl inositol-3 kinases, myo-inositol signaling, and Ras oncogenes.

Several protein tyrosine kinases catalyse the phosphorylation of specific tyrosyl residues in various proteins involved in the regulation of cell growth. Such protein tyrosine kinases can be broadly classified as receptor or non-receptor kinases.

Receptor tyrosine kinases are transmembrane proteins having an extracellular ligand binding domain, a transmembrane domain, and a tyrosine kinase domain. Receptor tyrosine kinases are involved in the regulation of cell growth and are generally termed growth factor receptors. Inappropriate or uncontrolled activation of many of these kinases, i.e. aberrant kinase growth factor receptor activity, for example by over-expression or mutation, has been shown to result in uncontrolled cell growth. Accordingly, the aberrant activity of such kinases has been linked to malignant tissue growth. Consequently, inhibitors of such kinases could provide cancer treatment methods. Growth factor receptors include, for example, epidermal growth factor receptor (EGFr), platelet derived growth factor receptor (PDGFr), erbB2, erbB4, vascular endothelial growth factor receptor (VEGFr), tyrosine kinase with immunoglobulin-like and epidermal growth factor homology domains (TIE-2), insulin growth factor-I (IGFI) receptor, macrophage colony stimulating factor (cfms), BTK, ckit, cmet, fibroblast growth factor (FGF) receptors, Trk receptors (TrkA, TrkB, and TrkC), ephrin (eph) receptors, and the RET protooncogene. Several inhibitors of growth receptors are under development and include ligand antagonists, antibodies, tyrosine kinase inhibitors and anti-sense oligonucleotides. Growth factor receptors and agents that inhibit growth factor receptor function are described, for instance, in Kath, John C., Exp. Opin. Ther. Patents (2000) 10(6):803-818; Shawver et al DDT Vol 2, No. 2 Feb. 1997; and Lofts, F. J. et al, "Growth factor receptors as targets", New Molecular Targets for Cancer Chemotherapy, ed. Workman, Paul and Kerr, David, CRC press 1994, London.

Tyrosine kinases, which are not growth factor receptor kinases are termed non-receptor tyrosine kinases. Non-receptor tyrosine kinases for use in the present invention, which are targets or potential targets of anti-cancer drugs, include cSrc, Lck, Fyn, Yes, Jak, cAbl, FAK (Focal adhesion kinase), Brutons tyrosine kinase, and Bcr-Abl. Such non-receptor kinases and agents which inhibit non-receptor tyrosine kinase function are described in Sinh, S, and Corey, S. J., (1999) Journal of Hematotherapy and Stem Cell Research 8 (5): 465-80; and Bolen, J. B., Brugge, J. S., (1997) Annual review of Immunology. 15: 371-404.

SH2/SH3 domain blockers are agents that disrupt SH2 or SH3 domain binding in a variety of enzymes or adaptor proteins including, PI3-K p85 subunit, Src family kinases, adaptor molecules (Shc, Crk, Nck, Grb2) and Ras-GAP. SH2/SH3 domains as targets for anti-cancer drugs are discussed in Smithgall, T. E. (1995), Journal of Pharmacological and Toxicological Methods. 34(3) 125-32.

Inhibitors of Serine/Threonine Kinases including MAP kinase cascade blockers which include blockers of Raf kinases (rafk), Mitogen or Extracellular Regulated Kinase (MEKs), and Extracellular Regulated Kinases (ERKs); and Protein kinase C family member blockers including blockers of PKCs (alpha, beta, gamma, epsilon, mu, lambda, iota, zeta). IkB kinase family (IKKa, IKKb), PKB family kinases, akt kinase family members, and TGF beta receptor kinases. Such Serine/Threonine kinases and inhibitors thereof are described in Yamamoto, T., Taya, S., Kaibuchi, K., (1999), Journal of Biochemistry. 126 (5) 799-803; Brodt, P, Samani, A., and Navab, R. (2000), Biochemical Pharmacology, 60. 1101-1107; Massague, J., Weis-Garcia, F. (1996) Cancer Surveys. 27:41-64; Philip, P. A., and Harris, A. L. (1995), Cancer Treatment and Research. 78: 3-27, Lackey, K. et al Bioorganic and Medicinal Chemistry Letters, (10), 2000, 223-226; U.S. Pat. No. 6,268,391; and Martinez-Iacaci, L., et al, Int. J. Cancer (2000), 88(1), 44-52.

Inhibitors of Phosphotidyl inositol-3 Kinase family members including blockers of PI3-kinase, ATM, DNA-PK, and Ku may also be useful in the present invention. Such kinases are discussed in Abraham, R. T. (1996), Current Opinion in Immunology. 8 (3) 412-8; Canman, C. E., Lim, D. S. (1998), Oncogene 17 (25) 3301-3308; Jackson, S. P. (1997), International Journal of Biochemistry and Cell Biology. 29 (7):935-8; and Zhong, H. et al, Cancer res, (2000) 60(6), 1541-1545.

Also of interest in the present invention are Myo-inositol signaling inhibitors such as phospholipase C blockers and Myoinositol analogues. Such signal inhibitors are described in Powis, G., and Kozikowski A., (1994) New Molecular Targets for Cancer Chemotherapy ed., Paul Workman and David Kerr, CRC press 1994, London.

Another group of signal transduction pathway inhibitors are inhibitors of Ras Oncogene. Such inhibitors include inhibitors of farnesyltransferase, geranyl-geranyl transferase, and CAAX proteases as well as anti-sense oligonucleotides, ribozymes and immunotherapy. Such inhibitors have been shown to block ras activation in cells containing wild type mutant ras, thereby acting as antiproliferation agents. Ras oncogene inhibition is discussed in Scharovsky, O. G., Rozados, V. R., Gervasoni, S. I. Matar, P. (2000), Journal of Biomedical Science. 7(4) 292-8; Ashby, M. N. (1998), Current Opinion in Lipidology. 9 (2) 99-102; and BioChim. Biophys. Acta, (19899) 1423(3):19-30.

As mentioned above, antibody antagonists to receptor kinase ligand binding may also serve as signal transduction inhibitors. This group of signal transduction pathway inhibitors includes the use of humanized antibodies to the extracellular ligand binding domain of receptor tyrosine kinases. For example Imclone C225 EGFR specific antibody (see Green, M. C. et al, Monoclonal Antibody Therapy for Solid Tumors, Cancer Treat. Rev., (2000), 26(4), 269-286); Herceptin® erbB2 antibody (see Tyrosine Kinase Signalling in Breast cancer:erbB Family Receptor Tyrosine Kinases, Breast cancer Res., 2000, 2(3), 176-183); and 2CB VEGFR2 specific antibody (see Brekken, R. A. et al, Selective Inhibition of VEGFR2 Activity by a monoclonal Anti-VEGF antibody blocks tumor growth in mice, Cancer Res. (2000) 60, 5117-5124).

Non-receptor kinase angiogenesis inhibitors may also be useful in the present invention. Inhibitors of angiogenesis related VEGFR and TIE2 are discussed above in regard to signal transduction inhibitors (both receptors are receptor tyrosine kinases). Angiogenesis in general is linked to erbB2/EGFR signaling since inhibitors of erbB2 and EGFR have been shown to inhibit angiogenesis, primarily VEGF expression. Accordingly, non-receptor tyrosine kinase inhibitors may be used in combination with the compounds of the present invention. For example, anti-VEGF antibodies, which do not recognize VEGFR (the receptor tyrosine kinase), but bind to the ligand; small molecule inhibitors of integrin (alpha$_v$ beta$_3$) that will inhibit angiogenesis; endostatin and angiostatin (non-RTK) may also prove useful in combination with the disclosed compounds. (See Bruns C J et al (2000), Cancer Res., 60: 2926-2935; Schreiber A B, Winkler M E, and Derynck R. (1986), Science, 232: 1250-1253; Yen L et al. (2000), Oncogene 19: 3460-3469).

Agents used in immunotherapeutic regimens may also be useful in combination with the compounds of formula (I). There are a number of immunologic strategies to generate an immune response. These strategies are generally in the realm of tumor vaccinations. The efficacy of immunologic approaches may be greatly enhanced through combined inhibition of signaling pathways using a small molecule vaccine inhibitor. Discussion of the immunologic/tumor vaccine approach against erbB2/EGFR are found in Reilly R T et al. (2000), Cancer Res. 60: 3569-3576; and Chen Y, Hu D, Eling D J, Robbins J, and Kipps T J. (1998), Cancer Res. 58: 1965-1971.

Agents used in proapoptotic regimens (e.g., bcl-2 antisense oligonucleotides) may also be used in the combination of the present invention. Members of the Bcl-2 family of proteins block apoptosis. Upregulation of bcl-2 has therefore been linked to chemoresistance. Studies have shown that the epidermal growth factor (EGF) stimulates anti-apoptotic members of the bcl-2 family (i.e., mcl-1). Therefore, strategies designed to downregulate the expression of bcl-2 in tumors have demonstrated clinical benefit and are now in Phase II/III trials, namely Genta's G3139 bcl-2 antisense oligonucleotide. Such proapoptotic strategies using the antisense oligonucleotide strategy for bcl-2 are discussed in Water J S et al. (2000), J. Clin. Oncol. 18: 1812-1823; and Kitada S et al. (1994), Antisense Res. Dev. 4: 71-79.

Cell cycle signalling inhibitors inhibit molecules involved in the control of the cell cycle. A family of protein kinases called cyclin dependent kinases (CDKs) and their interaction with a family of proteins termed cyclins controls progression through the eukaryotic cell cycle. The coordinate activation and inactivation of different cyclin/CDK complexes is necessary for normal progression through the cell cycle. Several inhibitors of cell cycle signalling are under development. For instance, examples of cyclin dependent kinases, including CDK2, CDK4, and CDK6 and inhibitors for the same are described in, for instance, Rosania et al, Exp. Opin. Ther. Patents (2000) 10(2):215-230.

In one embodiment, the cancer treatment method of the claimed invention includes the co-administration a compound of formula I and/or a pharmaceutically acceptable salt, hydrate, solvate or pro-drug thereof and at least one anti-neoplastic agent, such as one selected from the group consisting of anti-microtubule agents, platinum coordination complexes, alkylating agents, antibiotic agents, topoisomerase II inhibitors, antimetabolites, topoisomerase I inhibitors, hormones and hormonal analogues, signal transduction pathway inhibitors, non-receptor tyrosine kinase angiogenesis inhibitors, immunotherapeutic agents, proapoptotic agents, and cell cycle signaling inhibitors.

Because the pharmaceutically active compounds of the present invention are active as AKT inhibitors they exhibit therapeutic utility in treating cancer and arthritis.

Suitably, the present invention relates to a method for treating or lessening the severity of a cancer selected from brain (gliomas), glioblastomas, leukemias, Bannayan-Zonana syndrome, Cowden disease, Lhermitte-Duclos disease, breast, colon, head and neck, kidney, lung, liver, melanoma, ovarian, pancreatic, prostate, sarcoma and thyroid.

Suitably, the present invention relates to a method for treating or lessening the severity of a cancer selected from breast, ovarian, pancreatic and prostate.

Isolation and Purification of His-Tagged AKT1 (aa 136-480)

Insect cells expressing His-tagged AKT1 (aa 136-480) were lysed in 25 mM HEPES, 100 mM NaCl, 20 mM imidazole; pH 7.5 using a polytron (5 mLs lysis buffer/g cells). Cell debris was removed by centrifuging at 28,000×g for 30 minutes. The supernatant was filtered through a 4.5-micron filter then loaded onto a nickel-chelating column pre-equilibrated with lysis buffer. The column was washed with 5 column volumes (CV) of lysis buffer then with 5 CV of 20% buffer B, where buffer B is 25 mM HEPES, 100 mM NaCl, 300 mM imidazole; pH 7.5. His-tagged AKT1 (aa 136-480) was eluted with a 20-100% linear gradient of buffer B over 10 CV. His-tagged AKT1 (136-480) eluting fractions were pooled and diluted 3-fold with buffer C, where buffer C is 25 mM HEPES, pH 7.5. The sample was then chromatographed over a Q-Sepharose HP column pre-equilibrated with buffer C. The column was washed with 5 CV of buffer C then step eluted with 5 CV 10% D, 5 CV 20% D, 5 CV 30% D, 5 CV 50% D and 5 CV of 100% D; where buffer D is 25 mM HEPES, 1000 mM NaCl; pH 7.5. His-tagged AKT1 (aa 136-480) containing fractions were pooled and concentrated in a 10-kDa molecular weight cutoff concentrator. His-tagged AKT1 (aa 136480) was chromatographed over a Superdex 75 gel filtration column pre-equilibrated with 25 mM HEPES, 200 mM NaCl, 1 mM DTT; pH 7.5. His-tagged AKT1 (aa 136-480) fractions were examined using SDS-PAGE and mass spec. The protein was pooled, concentrated and frozen at −80° C.

His-tagged AKT2 (aa 138-481) and His-tagged AKT3 (aa 135-479) were isolated and purified in a similar fashion.

His-Tagged AKT Enzyme Assay

Compounds of the present invention were tested for AKT 1, 2, and 3 protein serine kinase inhibitory activity in substrate phosphorylation assays. This assay examines the ability of small molecule organic compounds to inhibit the serine phosphorylation of a peptide substrate. The substrate phosphorylation assays use the catalytic domains of AKT 1, 2, or 3. AKT 1, 2 and 3 are also commercially available from Upstate USA, Inc. The method measures the ability of the isolated enzyme to catalyze the transfer of the gamma-phosphate from ATP onto the serine residue of a biotinylated synthetic peptide SEQ. ID NO: 1 (Biotin-ahx-ARKRERAYSFGHHA-amide). Substrate phosphorylation was detected by the following procedure:

Assays were performed in 384 well U-bottom white plates. 10 nM activated AKT enzyme was incubated for 40 minutes at room temperature in an assay volume of 20 ul containing 50 mM MOPS, pH 7.5, 20 mM $MgCl_2$, 4 uM ATP, 8 uM peptide, 0.04 uCi [g-$^{33}$P] ATP/well, 1 mM CHAPS, 2 mM DTT, and 1 ul of test compound in 100% DMSO. The reaction was stopped by the addition of 50 ul SPA bead mix (Dulbecco's PBS without $Mg^{2+}$ and $Ca^{2+}$, 0.1% Triton X-100, 5 mM EDTA, 50 uM ATP, 2.5 mg/ml Streptavidin-coated SPA beads.) The plate was sealed, the beads were allowed to settle overnight, and then the plate was counted in a Packard Topcount Microplate Scintillation Counter (Packard Instrument Co., Meriden, Conn.).

The data for dose responses were plotted as % Control calculated with the data reduction formula 100*(U1−C2)/(C1−C2) versus concentration of compound where U is the unknown value, C1 is the average control value obtained for DMSO, and C2 is the average control value obtained for 0.1M EDTA. Data are fitted to the curve described by: y=((Vmax*x)/(K+x)) where Vmax is the upper asymptote and K is the IC50.

Cloning of Full-Length Human (FL) AKT1:

Full-length human AKT1 gene was amplified by PCR from a plasmid containing myristylated-AKT1-ER (gift from Robert T. Abraham, Duke University under MTA, described in Klippel et al. in Molecular and Cellular Biology 1998 Volume 18 p. 5699) using the 5' primer: SEQ. ID NO: 2 5' TATATAGGATCCATGAGCGACGTGGC 3' and the 3' primer: SEQ. ID NO: 3 AAATTTCTCGAGTCAGGCCGTGCTGCTGG 3'. The 5' primer included a BamHI site and the 3' primer included an XhoI site for cloning purposes. The resultant PCR product was subcloned in pcDNA3 as a BamHI/XhoI fragment. A mutation in the sequence (TGC) coding for a Cysteine[25] was converted to the wild-type AKT1 sequence (CGC) coding for an Arginine[25] by site-directed mutagenesis using the QuikChange® Site Directed Mutagenesis Kit (Stratagene). The AKT1 mutagenic primer: SEQ. ID NO: 4 5' ACCTGGCGGCCACGCTACTTCCTCC and selection primer: SEQ. ID NO: 5 5' CTCGAGCATGCMCTA-GAGGGCC (designed to destroy an XbaI site in the multiple cloning site of pcDNA3) were used according to manufacturer's suggestions. For expression/purification purposes, AKT1 was isolated as a BamHI/XhoI fragment and cloned into the BamHI/XhoI sites of pFastbacHTb (Invitrogen).

Expression of FL Human AKT1:

Expression was done using the BAC-to-BAC Baculovirus Expression System from Invitrogen (catalog #10359-016). Briefly 1) the cDNA was transferred from the FastBac vector into bacmid DNA, 2) the bacmid DNA was isolated and used to transfect Sf9 insect cells, 3) the virus was produced in Sf9 cells, 4) T. ni cells were infected with this virus and sent for purification.

Purification of FL Human AKT1:

For the purification of full-length AKT1, 130 g sf9 cells (batch # 41646W02) were resuspended in lysis buffer (buffer A, 1 L, pH 7.5) containing 25 mM HEPES, 100 mM NaCl, and 20 mM imidazole. The cell lysis was carried out by Avestin (2 passes at 15K-20K psi). Cell debris was removed by centrifuging at 16K rpm for 1 hour and the supernatant was batch bound to 10 ml Nickel Sepharose HP beads at 4 C for over night. The beads were then transferred to column and the bound material was eluted with buffer B (25 mM HEPES, 100 mM NaCl, 300 mM imidazole, pH 7.5). AKT eluting fractions were pooled and diluted 3 fold using buffer C (25 mM HEPES, 5 mM DTT; pH 7.5). The sample was filtered and chromatographed over a 10 mL Q-HP column pre-equilibrated with buffer C at 2 mL/min.

The Q-HP column was washed with 3 column volume (CV) of buffer C, then step eluted with 5 CV 10% D, 5 CV 20% D, 5 CV 30% D, 5 CV 50% D and 5 CV of 100% D; where buffer D is 25 mM HEPES, 1000 mM NaCl, 5 mM DTT; pH 7.5. 5 mL fractions collected. AKT containing fractions were pooled and concentrated to 5 ml. The protein was next loaded to a 120 ml Superdex 75 sizing column that was pre-equilibrated with 25 mM HEPES, 200 mM NaCl, 5 mM DTT; pH 7.5. 2.5 mL fractions were collected.

AKT 1 eluting fractions were pooled, aliquoted (1 ml) and stored at −80 C. Mass spec and SDS-PAGE analysis were used to confirm purity and identity of the purified full-length AKT1.

Full-length (FL) AKT2 and (FL) AKT3 were isolated and purified in a similar fashion.

Full-Length AKT Enzyme Assay

Compounds of the present invention were tested for AKT 1, 2, and 3 protein serine kinase inhibitory activity in substrate phosphorylation assays. This assay examines the ability of small molecule organic compounds to inhibit the serine phosphorylation of a peptide substrate. The substrate phosphorylation assays use the catalytic domains of AKT 1, 2, or 3. The method measures the ability of the isolated enzyme to catalyze the transfer of the gamma-phosphate from ATP onto the serine residue of a biotinylated synthetic peptide SEQ. ID NO: 1 (Biotin-ahx-ARKRERAYSFGHHA-amide). Substrate phosphorylation was detected by the following procedure.

Assays were performed in 384 well U-bottom white plates. 10 nM activated AKT enzyme was incubated for 40 minutes at room temperature in an assay volume of 20 ul containing 50 mM MOPS, pH 7.5, 20 mM $MgCl_2$, 4 uM ATP, 8 uM peptide, 0.04 uCi [g-33P] ATP/well, 1 mM CHAPS, 2 mM DTT, and 1 ul of test compound in 100% DMSO. The reaction was stopped by the addition of 50 ul SPA bead mix (Dulbecco's PBS without $Mg^{2+}$ and $Ca^{2+}$, 0.1% Triton X-100, 5 mM EDTA, 50 uM ATP, 2.5 mg/ml Streptavidin-coated SPA beads.) The plate was sealed, the beads were allowed to settle overnight, and then the plate was counted in a Packard Topcount Microplate Scintillation Counter (Packard Instrument Co., Meriden, Conn.). The data for dose responses were plotted as % Control calculated with the data reduction formula 100*(U1−C2)/(C1−C2) versus concentration of compound where U is the unknown value, C1 is the average control value obtained for DMSO, and C2 is the average control value obtained for 0.1M EDTA. Data are fitted to the curve described by: $y=((Vmax*x)/(K+x))$ where Vmax is the upper asymptote and K is the IC50.

After several trials, the compound of Example 1 demonstrated an average $IC_{50}$ (uM) activity of: 0.002 um, FL AKT1; 0.013 um, FL AKT2; and 0.009 um, FL AKT3 in the above full-length AKT enzyme assay.

Activity against tumor cell lines and a normal cell line and the solubilities of the compounds of Examples 1 to 10 of this invention were compared to what is considered to be the most structurally related compounds prepared in International Application No. PCT/US2004/024340. Specifically, the compound of Example 140 in International Application No. PCT/US2004/024340 (compound 4-(1-ethyl-7-{[3-(4-morpholinyl)propyl]oxy}-4-phenyl-1H-imidazo[4,5-c]pyridin-2-yl)-1,2,5-oxadiazol-3-amine trifluoroacetate, hereinafter Compound R), the compound of Example 151 in International Application No. PCT/US2004/024340 (compound 1-{[2-(4-amino-1,2,5-oxadiazol-3-yl)-1-ethyl-4-phenyl-1H-imidazo[4,5-c]pyridin-7-yl]oxy}-3-(4-morpholinyl)-2-propanol trifluoroacetate, hereinafter Compound S), the compound of Example 152 in International Application No. PCT/US2004/024340 (compound 4-(1-ethyl-7-{[2-(4-morpholinyl)ethyl]oxy}-4-phenyl-1H-imidazo[4,5-c]pyridin-2-yl)-1,2,5-oxadiazol-3-amine trifluoroacetate, hereinafter Compound T), the compound of Example 17 in International Application No. PCT/US2004/024340 (compound 4-[1-ethyl-7-(piperidin-4-yloxy)-1H-imidazo[4,5-c]pyridine-2-yl]-furazan-3-ylamine trifluoroacetate, hereinafter Compound U), the compound of Example 127 in International Application No. PCT/US2004/024340 (compound: 4-{1-ethyl-4-phenyl-7-[(3-piperidinylmethyl)oxy]-1H-imidazo-[4,5-c]pyridin-2-yl}-1,2,5-oxadiazol-3-amine trifluoroacetate, hereinafter Compound V), the compound of Example 215 in International Application No. PCT/US2004/024340 (compound 4-[7-[(4-aminobutyl)oxy]-2-(4-amino-1,2,5-oxadiazol-3-yl)-1-ethyl-1H-imidazo[4,5-c]pyridin-4-yl]-2-methyl-3-butyn-2-ol trifluoroacetate, hereinafter Compound W), the compound of Example 222 in International Application No. PCT/US2004/024340 (compound 4-{2-(4-amino-1,2,5-oxadiazol-3-yl)-7-[(3-aminopropyl)oxy]-1-ethyl-1H-imidazo[4,5-c]pyridin-4-yl}-2-methyl-3-butyn-2-ol trifluoroacetate, hereinafter Compound X), the compound of Example 223 in International Application No. PCT/US2004/024340 (compound: 4-{2-(4-amino-1,2,5-oxadiazol-3-yl)-1-ethyl-7-[(4-piperidinylmethyl)oxy]-1H-imidazo[4,5-c]pyridin-4-yl}-2-methyl-3-butyn-2-ol trifluoroacetate, hereinafter Compound Y) and the compound of Example 265 in International Application No. PCT/US2004/024340 (compound: 4-(2-(4-amino-1,2,5-oxadiazol-3-yl)-1-ethyl-7-{[3-({2-[4-(methyloxy)phenyl]ethyl}amino)propyl]oxy}-1H-imidazo[4,5-c]pyridin-4-yl)-2-methyl-3-butyn-2-ol, hereinafter Compound Z).

Compounds R, S, T, U, V, W, X, Y and Z can be prepared as described in International Application No. PCT/US2004/024340.

Cellular Assays Methylene Blue Growth Inhibition Assay

Tumor cell lines used in this assay were BT474 (human breast carcinoma) and LNCaP (lymph node metastasis of prostate cancer). HFF (normal human foreskin fibroblast) was also included. All cell lines were cultured in RPMI 1640 media (Invitrogen Corporation 22400-071) containing 10% Fetal Bovine Serum (FBS) at 37° C. in a humidified 5% $CO_2$ incubator. Cells were harvested using trypsin/EDTA, counted using a hemacytometer and plated in 96-well tissue culture plates (Costar 35-3075), 100 uL per well, at the following densities: BT474 15,000 cells/well, LNCaP 5,000 cells/well and HFF 5,000 cells/well. 10 mM stocks of compounds in DMSO were serially diluted in DMSO through nine 3-fold dilutions in 96-well plates (Costar Corning 3363), and stored at −80 C. The next day, compound dilutions were thawed and 4 uL of each transferred to 662 uL RPMI 1640+100 ug/mL gentamicin, resulting in twice the final required test concentrations. 100 uL of compounds diluted in RPMI 1640 were added to all cell lines. The final concentration of DMSO in all wells, including controls, was 0.3%. Cells were incubated at 37 C, 5% CO2 for 3 days. Medium was removed by aspiration. Cell biomass was estimated by staining cells with 80 uL methylene blue (Sigma M9140, 0.5% in 50:50 ethanol:water), and incubating at room temperature for 1 hour. Stain was aspirated and the plates rinsed by immersion in water, then air-dried. Stain was released from cells by adding 100 uL of solubilizing solution (1% N-lauroyl sarcosine, sodium salt, Sigma L5125, in PBS) and incubating at room temperature for at least 30 minutes. Plates were shaken and the optical density at 620 nm was measured on a microplate reader. Percent inhibition of cell growth was calculated relative to vehicle-treated control wells. Concentration of compound that inhibits 50% of cell growth ($IC_{50}$) was interpolated using non-linear regression (Levenberg-Marquadt) and the equation, $y=Vmax*(1-(x^n/K^n+x^n)))+Y2$. [Ref: Mager, M. E. (1972) Data Analysis in Biochemistry and Biophysics. New York: Academic Press]

| Examples | Methylene Blue Growth Inhibition Assay, IC50 (uM) | | | |
| --- | --- | --- | --- | --- |
| | BT474 (human breast carcinoma) | LNCaP (lymph node metastasis of prostate cancer) | HFF (normal human foreskin fibroblast) | Solubility in 50 mM phosphate buffer at pH 7.4 (uM) |
| Compound R | 17.71 | 1.42 | 19.9 | 0 |
| Compound S | >30 | 7.77 | >30 | Not tested |
| Compound T | >30 | >30 | 18.9 | 0 |
| Compound U | 4.51 | | 6.47 | 200 |
| Compound V | 1.870 | 1.640 | 0.57 | 9 |
| Compound W | 8.211 | 0.836 | 22.07 | 210 |
| Compound X | 0.241 | 0.258 | 18.147 | 173 |
| Compound Y | 2.593 | 0.217 | >30 | 159 |
| Compound Z | 0.266 | 0.048 | 5.507 | 37 |
| Example 1 | 0.484 | 0.016 | >20 | 210 |
| Example 2 | 1.00 | 0.189 | >30 | 188 |
| Example 3 | 0.006 | 0.004 | >30 | 110 |
| Example 4 | 0.037 | 0.015 | >25 | 154 |
| Example 5 | 1.032 | 0.459 | 20.1 | 83 |
| Example 6 | 0.324 | 0.053 | 16.8 | 44 |
| Example 7 | 0.186 | 0.083 | >30 | 23 |
| Example 8 | 0.665 | 0.272 | >30 | 34 |
| Example 9 | 0.080 | 0.049 | 9.39 | 129 |
| Example 10 | No tested | Not tested | Not tested | 6 |

The pharmaceutically active compounds within the scope of this invention are useful as AKT inhibitors in mammals, particularly humans, in need thereof.

The present invention therefore provides a method of treating cancer, arthritis and other conditions requiring AKT inhibition, which comprises administering an effective amount of a compound of Formula (I) or a pharmaceutically acceptable salt, hydrate, solvate or pro-drug thereof. The compounds of Formula (I) also provide for a method of treating the above indicated disease states because of their demonstrated ability to act as Akt inhibitors. The drug may be administered to a patient in need thereof by any conventional route of administration, including, but not limited to, intravenous, intramuscular, oral, subcutaneous, intradermal, and parenteral.

The pharmaceutically active compounds of the present invention are incorporated into convenient dosage forms such as capsules, tablets, or injectable preparations. Solid or liquid pharmaceutical carriers are employed. Solid carriers include, starch, lactose, calcium sulfate dihydrate, terra alba, sucrose, talc, gelatin, agar, pectin, acacia, magnesium stearate, and stearic acid. Liquid carriers include syrup, peanut oil, olive oil, saline, and water. Similarly, the carrier may include any prolonged release material, such as glyceryl monostearate or glyceryl distearate, alone or with a wax. The amount of solid carrier varies widely but, preferably, will be from about 25 mg to about 1 g per dosage unit. When a liquid carrier is used, the preparation will, for example, be in the form of a syrup, elixir, emulsion, soft gelatin capsule, sterile injectable liquid such as an ampoule, or an aqueous or nonaqueous liquid suspension.

The pharmaceutical preparations are made following conventional techniques of a pharmaceutical chemist involving mixing, granulating, and compressing, when necessary, for tablet forms, or mixing, filling and dissolving the ingredients, as appropriate, to give the desired oral or parenteral products.

Doses of the presently invented pharmaceutically active compounds in a pharmaceutical dosage unit as described above will be an efficacious, nontoxic quantity preferably selected from the range of 0.001-100 mg/kg of active compound, preferably 0.001-50 mg/kg. When treating a human patient in need of an Akt inhibitor, the selected dose is administered preferably from 1-6 times daily, orally or parenterally. Preferred forms of parenteral administration include topically, rectally, transdermally, by injection and continuously by infusion. Oral and/or parenteral dosage units for human administration preferably contain from 0.05 to 3500 mg of active compound.

Optimal dosages to be administered may be readily determined by those skilled in the art, and will vary with the particular Akt inhibitor in use, the strength of the preparation, the mode of administration, and the advancement of the disease condition. Additional factors depending on the particular patient being treated will result in a need to adjust dosages, including patient age, weight, diet, and time of administration.

The method of this invention of inducing Akt inhibitory activity in mammals, including humans, comprises administering to a subject in need of such activity an effective Akt inhibiting amount of a pharmaceutically active compound of the present invention.

The invention also provides for the use of a compound of Formula (I) in the manufacture of a medicament for use as an Akt inhibitor.

The invention also provides for the use of a compound of Formula (I) in the manufacture of a medicament for use in therapy.

The invention also provides for the use of a compound of Formula (I) in the manufacture of a medicament for use in treating cancer.

The invention also provides for the use of a compound of Formula (I) in the manufacture of a medicament for use in treating arthritis.

The invention also provides for a pharmaceutical composition for use as an Akt inhibitor which comprises a compound of Formula (I) and a pharmaceutically acceptable carrier.

The invention also provides for a pharmaceutical composition for use in the treatment of cancer which comprises a compound of Formula (I) and a pharmaceutically acceptable carrier.

The invention also provides for a pharmaceutical composition for use in treating arthritis which comprises a compound of Formula (I) and a pharmaceutically acceptable carrier.

No unacceptable toxicological effects are expected when compounds of the invention are administered in accordance with the present invention.

In addition, the pharmaceutically active compounds of the present invention can be co-administered with further active ingredients, such as other compounds known to treat cancer or arthritis, or compounds known to have utility when used in combination with an Akt inhibitor.

Without further elaboration, it is believed that one skilled in the art can, using the preceding description, utilize the present invention to its fullest extent. The following Examples are, therefore, to be construed as merely illustrative and not a limitation of the scope of the present invention in any way.

EXPERIMENTAL DETAILS

The compounds of Examples 1 to 10 are readily made according to Scheme 1 or by analogous methods.

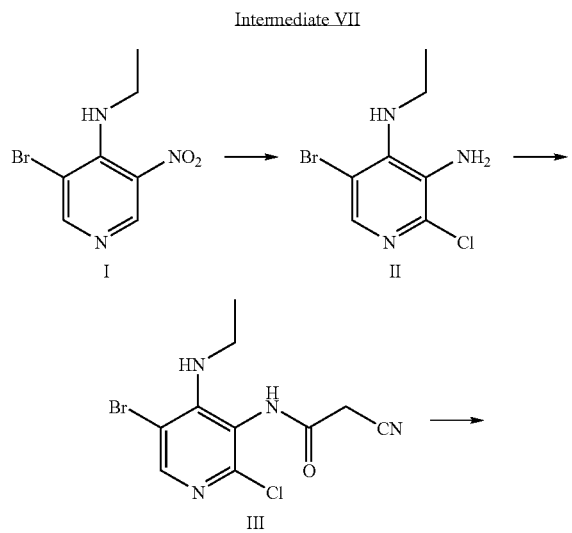

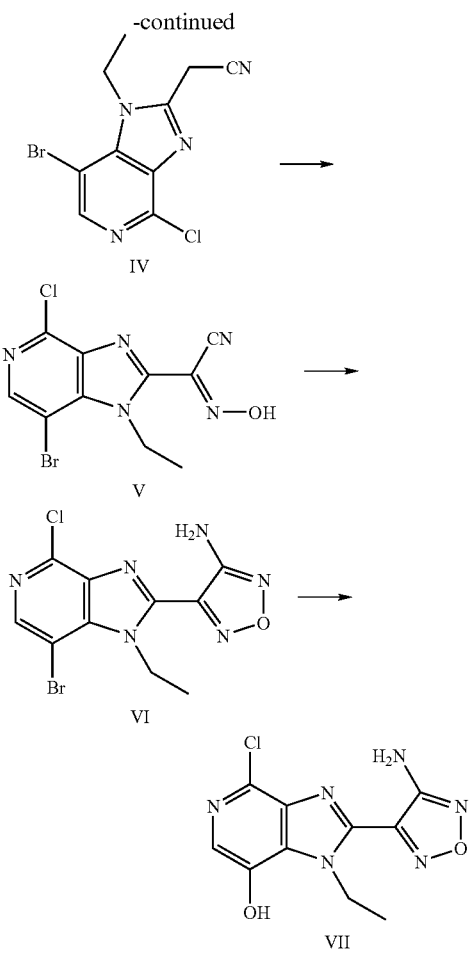

Preparation of 2-(4-amino-1,2,5-oxadiazol-3-yl)-4-chloro-1-ethyl-1H-imidazo[4,5-c]pyridin-7-ol a) 5-Bromo-2-chloro-$N^4$-ethyl-pyridine-3,4-diamine (II)

3-Bromo-5-nitropyridin-4-yl)amine (I, 700 g, 2.86 mol) was dissolved in conc HCl (7 L) and heated to 85° C. Tin (II) chloride (1626 g, 8.58 mol) was added in portions. The reaction was heated at reflux for 1 h and then allowed to cool to ambient temperature overnight. The resulting yellow precipitate was collected by filtration, suspended in ice water (5 L) and the mixture was adjusted to pH 12 with 12N NaOH. The resulting solution was extracted with $CH_2Cl_2$ (2×4 L) and the combined organic extracts were dried over $Na_2SO_4$. The solvent was removed under reduced pressure to give 550 g (77% yield) of the desired compound (II). This was used in the next step without further purification. MS (ES+) m/z 250 (M+H)⁺.

b) N-[5-Bromo-2-chloro-4-(ethylamino)-3-pyridinyl]-2-cyanoacetamide (III)

To a solution of 5-bromo-2-chloro-$N^4$-ethyl-pyridine-3,4-diamine (II, 550 g, 2.21 mol) in $CH_2Cl_2$ (5.5 L) was added 1-(3-dimethylaminopropyl)-3-ethylcarbodiimide hydrochloride (634.5 g, 3.31 mol), cyanoacetic acid (282 g, 3.31 mol) and N-methylmorpholine (897 g, 8.84 mol). A significant exotherm (~20° C.) was observed upon the addition of the 1-(3-dimethylaminopropyl)-3-ethylcarbodiimide hydrochloride and cyanoacetic acid. After stirring at ambient temperature for 2 h, the solvent was removed under reduced pressure. The resulting reside was extracted with warm EtOAc (40° C., 20 L) and water (40° C., 8 L). The aqueous layer was washed with addition EtOAc (10 L) and the combined organic extracts were washed with water (10 L). The organic extract was concentrated under reduced pressure to a slurry and filtered. The solid was washed with EtOAc and dried to give 534 g (76% yield) of the desired compound (III) as a white crystalline solid. This was used in the next step without further purification. MS (ES+) m/z 317 (M+H)+.

c) (7-Bromo-4-chloro-1-ethyl-1H-imidazo[4,5-c]pyridin-2-yl)-hydroxyimino-acetonitrile (V)

A solution of N-[5-bromo-2-chloro-4-(ethylamino)-3-pyridinyl]-2-cyanoacetamide III, (458 g, 1.45 mol) in glacial acetic acid (4.6 L) was heated to 100° C. After 3 h, LC/MS analysis indicated that the conversion to (7-bromo-4-chloro-1-ethyl-1H-imidazo[4,5-c]pyridin-2-yl)acetonitrile (IV) was completed. After allowing to cool to ambient temperature, the reaction was charged with sodium nitrate (230 g, 3.34 mol) in portions. Vigorous gas evolution and foaming was observed together with a ~10° C. exotherm. After stirring at ambient temperature for 16 h, the solid was collected by filtration and dried to a constant weight to give 545 g of the desired product (V) as a light yellow solid. This was used in the next step without further purification. MS (ES+) m/z 328 (M+H)+.

d) 4-(7-Bromo-4-chloro-1-ethyl-1H-imidazo[4,5-c]pyridin-2-yl)-1,2,5-oxadiazol-3-amine (VI)

To a mixture of (7-bromo-4-chloro-1-ethyl-1H-imidazo[4,5-c]pyridin-2-yl)hydroxyimino-acetonitrile (V, 545 g, 1.45 mol) in dioxane (5 L) was added triethylamine (1 L) and hydroxylamine (143 g, 55% in water). The reaction was heated at reflux for 6 h. After cooling the reaction to ambient temperature, the mixture was filtered and the filtrate concentrated under reduced pressure to give a brown solid. The solid was suspended in methanol (1 L) and the suspension was stirred at 65° C. for 0.5 h. The solid was collected by filtration and dried to give 321 g (70% yield) of the desired compound (VI). This was used in the next step without further purification. MS (ES+) m/z 343 (M+H)+.

e) 2-(4-Amino-1,2,5-oxadiazol-3-yl)-4-chloro-1-ethyl-1H-imidazo[4,5-c]pyridin-7-ol (VII)

A suspension of 4-(7-bromo-4-chloro-1-ethyl-1H-imidazo[4,5-c]pyridin-2-yl)-1,2,5-oxadiazol-3-amine (VI, 50 g, 0.14 mol) in THF (1 L) was cooled in a dry-ice/acetone bath until the internal temperature was below −75° C. Isopropyl magnesium chloride (225 mL, 2M in ether, 0.45 mol) was added slowly at a rate to keep the reaction temperature below −70° C. After an additional 10 min., trimethyl borate (54 mL, 0.48 mol) was added and the reaction was maintained in the dry-ice acetone bath for 1 h. The bath was removed and the reaction was allowed to reach ambient temperature. After 18 h., the resultant yellow suspension was cooled to 0° C. A solution of 30% hydrogen peroxide (250 mL) and 3N NaOH (100 mL) was added at a rate to keep the reaction temperature below 40° C. The ice bath was then removed and the reaction was stirred vigorously at ambient temperature for 2 h. The bulk of the organic solvent was removed under reduced pressure and the aqueous layer was acidified to pH 3 with 1N HCl. After stirring the resulting suspension for 30 min., ethyl acetate (200 mL) was added. After stirring for another 1 h, the solid was collected by filtration. The filter cake was washed sequentially with water, ethyl acetate, toluene and ethyl acetate. The solid was dried to a constant weight to give 35.9 g (88% yield) of the desired compound (VII) as a pale yellow solid. This was used without further purification. MS (ES+) m/z 281.3 (M+H)+.

Example 1

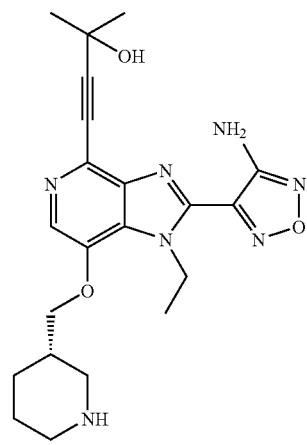

Preparation of 4-(2-(4-amino-1,2,5-oxadiazol-3-yl)-1-ethyl-7-{[(3S)-3-Piperidinylmethyl]oxy}-1H-imidazo[4,5-c]pyridin-4-yl)-2-methyl-3-butyn-2-ol a) 1,1-Dimethylethyl (3S)-3-(bromomethyl)-1-piperidinecarboxylate To a solution of 1,1-dimethylethyl (3S)-3-(hydroxymethyl)-1-piperidinecarboxylate (30.0 g, 139 mmol) and carbon tetrabromide (72.0 g, 217 mmol) in methylene chloride (150 mL) was added dropwise a solution of triphenyl phosphine (42.4 g, 162 mmol) in methylene chloride (150 mL). An ice-bath was used to maintain an internal temperature between 20 and 25° C. during the addition. After stirring the mixture at ambient temperature for 1 h, cyclohexane (500 mL) was added. Approximately one-half of the solvent was removed under reduced pressure. The remaining solution was cooled in an ice bath and the resulting precipitate was removed by filtration. The filtrate was concentrated under reduced pressure and the residue subjected to flash chromatography (0% to 25% ethyl acetate/hexanes, silica gel) to give 35.1 g (91% yield) of the desired product as a solid. MS (ES+) m/z 278 (M+H)+.

b) 1,1-Dimethylethyl 3-({[2-(4-amino-1,2,5-oxadiazol-3-yl)-4-chloro-1-ethyl-1H-imidazo[4,5-c]pyridin-7-yl]oxy}methyl)-1-piperidinecarboxylate A mixture consisting of the compound of intermediate VII (25.0 g, 89.1 mmol), cesium carbonate (41.0 g, 126 mmol) and the compound of Example 1(a) (35.0 g, 126 mmol) in DMF (200 mL) was stirred at 40° C. for 8 h and then at 35° C. for 18 h. The mixture was poured into rapidly stirring ice water (800 ml). After 10 min., ethyl acetate (300 mL) was added and the stirring continued for an additional 20 min. The solid was collected by filtration, washed with ethyl acetate (50 mL) and dried to give 36 g (85% yield) of the desired compound. MS (ES+) m/z 478 (M+H)+.

c) 1,1-Dimethylethyl 3-({[2-(4-amino-1,2,5-oxadiazol-3-yl)-1-ethyl-4-(3-hydroxy-3-methyl-1-butyn-1-yl)-1H-imidazo[4,5-c]pyridin-7-yl]oxy}methyl)-1-piperidinecarboxylate Two thick-walled pressure vessels were each charged with the compound of Example 1(b) (18 g, 37.7 mmol), 2-methyl-3-butyl-2-ol (8.0 mL, 82.5 mmol), (Ph3P)4Pd (0.5 g, 0.43 mmol), Zn dust (0.5 g., 7.4 mmol), NaI (1.1 g, 7.4 mmol), DBU (8 mL, 53.5 mmol), triethylamine (7.5 mL, 54.5 mmol) and DMSO (150 mL). Both vessels were purged with argon for 10 min then sealed and heated at 80° C. for 4 h. The mixture from one reaction vessel was poured into rapidly stirring ice water (1000 mL) and to the resulting mixture was added the contents of the remaining reaction vessel. After 10 min., ethyl acetate (300 mL) was added and stirring continued for an additional 20 min. The solid was collected by filtration, washed with ethyl acetate (50 mL) and dried to give 35.5 g (90% yield) of the desired compound. MS (ES+) m/z 526 (M+H)+.

d) 4-{2-(4-Amino-1,2,5-oxadiazol-3-yl)-1-ethyl-7-[(3-piperidinylmethyl)oxy]-1H-imidazo[4,5-c]pyridin-4-yl}-2-methyl-3-butyn-2-ol The compound of Example 1(c) (35.0 g, 66.6 mmol) and TFA (350 mL of a 20% solution in methylene chloride, 808 mmol) was stirred at ambient temperature for 2.5 h. The solution was poured slowly into rapidly stirring mixture of water, NaOH (36 g, 900 mmol), ethyl acetate (200 mL) and THF (1000 mL). The organic layer was separated and the aqueous layer was extracted with additional ethyl acetate/THF (1:5 v/v, 150 mL). The combined organic extract was washed with sat. NaCl, dried over Na2SO4. The solvent was removed under vacuum and the resulting solid was recrystallized from hot ethanol (1200 mL) to give 26.3 g (93% yield) of the title compound as a white crystalline solid. MS (ES+) m/z 426 (M+H)+.

Example 2

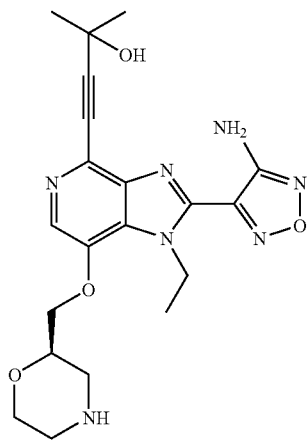

Preparation of 4-(2-(4-amino-1,2,5-oxadiazol-3-yl)-1-ethyl-7-{[(2R)-2-morpholinylmethyl]oxy}-1H-imidazo[4,5-c]pyridin-4-yl)-2-methyl-3-butyn-2-ol dihydrochloric acid salt a) 1,1-Dimethylethyl 2-(hydroxymethyl)-4-morpholinecarboxylate A solution of 4-{[(1,1-dimethylethyl)oxy]carbonyl}-2-morpholinecarboxylic acid (2.0 g, 21.6 mmol) in THF (45 mL) was cooled to 0° C. A solution of borane (39 mL, 39.0 mmol, 1M in THF) was added over 25 min via addition funnel. After warming to RT, the reaction was quenched by dropwise addition of methanol/acetic acid (18 mL, 9:1 v/v). The solvent was removed under reduced pressure and the residue partitioned between ethyl acetate and 1N HCl. The aqueous layer was extracted with ethyl acetate and combined extracts were washed with water, 1N NaOH, water, brine and dried over sodium sulfate. Removal of the solvent under reduced pressure afforded 1.83 g (97%) of the desired material. $^1$H NMR (400 MHz, CDCl$_3$) δ ppm 1.49 (s, 9H) 2.30 (br d, J=11.37 Hz, 1H) 2.69-2.79 (m, J=9.51, 6.41, 3.28, 3.28 Hz, 1H) 2.84 (ddd, J=13.77, 10.86, 3.16 Hz, 2H) 3.27-3.38 (m, 1H) 3.47 (br s, 1H) 3.63-3.75 (m, 2H) 4.10-4.19 (m, 1H) 4.27 (br s, 1H).

b) 1,1-dimethylethyl 2-{[(phenylcarbonyl)oxy]methyl}-4-morpholinecarboxylate (enantiomer E2)

To a stirred solution of 1,1-dimethylethyl 2-(hydroxymethyl)-4-morpholinecarboxylate (4.467 g, 21 mmol) in methylene chloride (58 mL) with pyridine (12 mL) and catalytic DMAP at 0° C. was added dropwise benzoyl chloride (3.18 g, 23 mmol). The reaction mixture was allowed to warm to room temperature and stirred 18 h. The reaction mixture was partitioned between 1 N HCl and methylene chloride. The aqueous layer washed with methylene chloride and the combined organic extract was washed with water then brine and dried over sodium sulfate. The solvent was removed under reduced pressure and the residue chromatographed on silica eluted with hexane/ethyl acetate to give 5.80 g (88%) of the racemic compound. This was resolved by chiral HPLC on a Chiralcel OD-H column (21×250 mm; 100 mg per injection) using a mobile phase of 90:10-heptane:ethanol to give the first eluting enantiomer E1 (2.85 g; >99% ee) and the second eluting enantiomer E2 (2.8 g; >99% ee) MS (ES+) m/z 322 (M+H)+.

c) 1,1-Dimethylethyl 2-(hydroxymethyl)-4-morpholinecarboxylate (enantiomer E2)

A solution of 1,1-dimethylethyl 2-{[(phenylcarbonyl)oxy]methyl}-4-morpholinecarboxylate (enantiomer E2) (1.08 g, 3.36 mmol) in methanol (30 mL) with 6N NaOH (5.6 mL. 33.6 mmol) was stirred at room temperature for 2 h. The methanol was removed under reduced pressure and the resulting mixture was partitioned between ethyl acetate and water. The organic extract was washed with brine, dried over sodium sulfate and solvent removed under reduced pressure to give the desired compound. 1H NMR (400 MHz, DMSO-d$_6$) d ppm 1.41 (s, 50H) 3.25-3.37 (m, 22H) 3.39-3.46 (m, 7H) 3.70 (d, J=12.88 Hz, 6H) 3.76-3.88 (m, 10H) 4.78 (t, J=5.68 Hz, 5H)

d) 1,1-dimethylethyl-2-(bromomethyl)-4-morpholinecarboxylate (enantiomer E2)

To a solution of the compound of Example 2(c) (0.67 g, 3.1 mmol) in dichloromethane (35 mL) at −20° C. was added CBr$_4$ (2.06 g, 6.17 mmol) followed by dropwise addition of a solution of PPh$_3$ (1.70 g, 6.48 mmol) in dichloromethane (25 mL). The reaction mixture was held at −15° C. for 18 h then stirred at room temperature for 1.5 h. The solvent was removed under reduced pressure and the residue purified by flash chromatography (silica gel, EtOAc/hexanes) gave 0.55 g (63%) of product that was used in the next step.

e) 1,1-Dimethylethyl-2-({[2-(4-amino-1,2,5-oxadiazol-3-yl)-4-chloro-1-ethyl-1H-imidazo[4,5-c]pyridin-7-yl]oxy}methyl)-4-morpholinecarboxylate (enantiomer E2)

The compound of intermediate VII (0.55 g, 1.95 mmol), the compound of Example 2(d) (0.546 g, 1.95 mmol) and cesium carbonate (1.92 g, 5.8 mmol) in DMF (35 mL) were stirred at 35° C. for 22 h. The product mixture was partitioned between ethyl acetate and water. The organic extracts were washed with brine and dried over sodium sulfate. The solvent was removed under reduced pressure to give 0.90 g (96%) of product that was used in the next step.

f) 4-(2-(4-amino-1,2,5-oxadiazol-3-yl)-1-ethyl-7-{[(2R)-2-morpholinylmethyl]oxy}-1H-imidazo[4,5-c]pyridin-4-yl)-2-methyl-3-butyn-2-ol dihydrochloric acid salt A thick-walled pressure vessel was charged with the compound of Example 2(e) (0.90 g, 1.87 mmol), DBU (0.84 mL, 5.6 mmol), Et$_3$N (0.57 mL, 5.6 mmol), NaI (0.084 g, 0.56 mmol), zinc dust (0.036 g, 0.56 mmol) 2-methyl-3-butyn-2-ol (0.47 g, 5.6 mmol), Pd(PPh$_3$)$_4$ (0.21 g, 0.19 mmol) and DMSO (60 mL). The pressure vessel was then sealed and heated at 80° C. for 1 h. After cooling to RT, the reaction was quenched by adding sat NH$_4$Cl. The aqueous layer was extracted with EtOAc and the combined extracts were washed with water, brine, and dried over sodium sulfate. The solvent was removed under reduced pressure and the residue subjected to flash chromatography (silica gel, MeOH/CH$_2$Cl$_2$) to give 1,1-dimethylethyl 2-({[2-(4-amino-1,2,5-oxadiazol-3-yl)-1-ethyl-4-(3-hydroxy-3-methyl-1-butyn-1-yl)-1H-imidazo[4,5-c]pyridin-7-yl]oxy}methyl)-4-morpholinecarboxylate. This was dissolved in methanol with ethereal HCl and left at room temperature for 18 h. A solid formed and was collected to give the product as the di-hydrochloride salt. MS (ES+) m/z 428 (M+H)$^+$. This was assigned the R-configuration by chiral HPLC comparison with the compound of Example (4).

Example 3

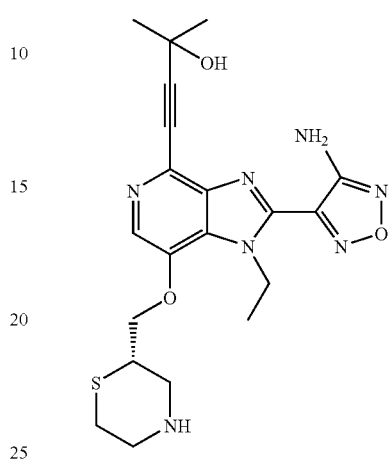

Preparation of 4-{2-(4-amino-1,2,5-oxadiazol-3-yl)-1-ethyl-7-[(2-thiomorpholinylmethyl)oxy]-1H-imidazo[4,5-c]pyridin-4-yl}-2-methyl-3-butyn-2-ol dihydrochloride (enantiomer E1)

a) 1,1-dimethylethyl 2-(hydroxymethyl)-4-thiomorpholinecarboxylate

A solution of 4-{2-[(1,1-dimethylethyl)oxy]-2-oxoethyl}-2-thiomorpholinecarboxylic acid (50.0 g, 0.202 mol) in THF (840 mL) was cooled to 0° C. A solution of borane (910 mL, 0.909 mol, 1M in THF) was added via addition funnel. The reaction was kept at 0° C. in the refrigerator overnight. The reaction was quenched with 10% acetic acid in methanol (420 ml) at 0° C. The solvent was removed under reduced pressure and the residue partitioned between ethyl acetate and 1N HCl. The aqueous layer was extracted with ethyl acetate and combined extracts were washed with water, 1N NaOH, water, brine and dried over sodium sulfate. Removal of the solvent under reduced pressure afforded 51.1 g of the desired material. This was used directly without further purification.

b) 1,1-dimethylethyl 2-{[(phenylcarbonyl)oxy]methyl}-4-thiomorpholinecarboxylate (enantiomer E1)

To stirred solution of 1,1-dimethylethyl 2-(hydroxymethyl)-4-thiomorpholinecarboxylate (51 g, 0.21 mol) in methylene chloride (550 ml) with pyridine (120 ml) and catalytic DMAP at 0 C was added dropwise benzoyl chloride (27.6 ml, 0.24 mol). The mixture was allowed to warm to room temperature and stirred overnight. The reaction was partitioned between 1N HCl and methylene chloride. The aqueous was washed with methylene chloride and combined organic extract was washed with water then brine and dried over sodium sulfate. The solvent was removed under reduced pressure and the residue chromatographed on silica eluted with hexane/ethyl acetate to give 60 g of the racemic compound. 60 g of racemate ((4-{2-[(1,1-dimethylethyl)oxy]-2-oxoethyl}-2-thiomorpholinyl)methyl benzoate was resolved by chiral HPLC on a Chiralpak AD, 20 micron (101.6×250 mm, 0.8 g per injection) using mobile phase 100% methanol to give first eluting enantiomer E1 (24.0 g, 5.7 min, 99% ee) and the second eluting enantiomer E2 (16.1 g, 6.8 min, 98% ee) MS (ES+) m/z 338 (M+H)+.

c) 1,1-dimethylethyl 2-(hydroxymethyl)-4-thiomorpholinecarboxylate (enantiomer E1)

A solution of compound Example 3(b) (13 g, 0.037 mol) in methanol (416 ml) with 6N NaOH (65 ml, 0.39 mol) was stirred at room temperature for 1 h. The methanol was removed under reduced pressure and the resulting mixture was partitioned between ethyl acetate and water. The organic extract was washed with brine, dried over sodium sulfate and solvent removed under reduced pressure to give 7.9 of the desired compound. $^1$H NMR (400 MHz, CHLOROFORM-D) d ppm 1.52 (s, 9H) 2.12 (s, 2H) 2.30 (s, 1H) 2.75 (s, 1H) 2.84 (s, 1H) 3.34 (s, 1H) 3.47 (s, 1H) 3.70 (s, 2H) 4.15 (s, 1H) 4.27 (s, 1H).

d) 1,1-dimethylethyl 2-(bromomethyl)-4-thiomorpholinecarboxylate (enantiomer E1)

To a solution of the compound of Example 3(c) (2.0 g, 8.57 mmol) in dichloromethane (96 mL) at −20° C. was added CBr$_4$ (5.74 g, 17.1 mmol) followed by dropwise addition of a solution of PPh$_3$ (4.72 g, 18.0 mmol) in dichloromethane (76 mL). After allowing the mixture to warm to RT, the solvent was removed under reduced pressure. Flash chromatography (silica gel, EtOAc/hexanes) gave 2.50 g of a material that was used directly without further purification.

e) 1,1-dimethylethyl 2-({[2-(4-amino-1,2,5-oxadiazol-3-yl)-4-chloro-1-ethyl-1H-imidazo[4,5-c]pyridin-7-yl]oxy}methyl)-4-thiomorpholinecarboxylate (enantiomer E1)

To a solution of the compound of intermediate VII (2.36 g, 8.40 mmol) in DMF (160 mL) was added anhydrous cesium carbonate (8.32 g, 25.0 mmol) and 1,1-dimethylethyl 2-(bromomethyl)-4-thiomorpholinecarboxylate (enantiomer E1) (2.50 g, 8.40 mmol). After stirring at ambient temperature for 4 h, sat NH4Cl was added and the reaction was extracted with EtOAc. The combined organic extracts were washed with water, brine and dried over sodium sulfate. The solvent was removed under reduced pressure and the residue subjected to flash chromatography (MeOH/CH2Cl2, silica gel) to give the 2.3 g of the desired compound contaminated with 1,1-dimethylethyl 7-{[2-(4-amino-1,2,5-oxadiazol-3-yl)-4-chloro-1-ethyl-1H-imidazo[4,5-c]pyridin-7-yl]oxy}tetrahydro-1,4-thiazepine-4-(5H)-carboxylate. This was used without further purification in the next step. MS (ES+) m/z 496 (M+H)+.

f) 4-{2-(4-amino-1,2,5-oxadiazol-3-yl)-1-ethyl-7-[(2-thiomorpholinylmethyl)oxy]-1H-imidazo[4,5-c]pyridin-4-yl}-2-methyl-3-butyn-2-ol (enantiomer E1)

A thick-walled pressure vessel was charged with 1,1-dimethylethyl 2-({[2-(4-amino-1,2,5-oxadiazol-3-yl)-4-chloro-1-ethyl-1H-imidazo[4,5-c]pyridin-7-yl]oxy}methyl)-4-thiomorpholinecarboxylate (enantiomer E1) (0.18 g, 1.35 mmol), Zn dust (0.03 g, 0.40 mmol), NaI (0.06 g, 0.40 mmol), DBU (0.61 mL, 4.00 mmol), TEA (0.56 mL, 4.00 mmol), 2-methyl-3-butyn-2-ol (0.48 mL, 5.70 mmol), (Ph$_3$P)$_4$Pd (0.08 g, 0.08 mmol) and dioxane (35 mL). After purging the mixture with nitrogen for 10 min., the vessel was sealed and heated at 80° C. for 2.5 h. After allowing the reaction to cool to ambient temperature, sat NH$_4$Cl was added and the reaction was extracted with EtOAc. The combined organic extracts were washed with water, brine and dried over sodium sulfate. The solvent was removed under reduced pressure and the residue subjected to flash chromatography (MeOH/CH$_2$Cl$_2$, silica gel). The Boc-protected product was dissolved in 25% TFA/CH$_2$Cl$_2$ (10 mL). After 30 min., the solvent was removed under reduced pressure. The residue was partitioned between 1N NaOH and ethyl acetate. The aqueous layer was extracted with additional ethyl acetate. The combined organic extracts were washed with brine, dried over sodium sulfate. The solvent was removed under reduced pressure. Flash chromatography (MeOH/CH$_2$Cl$_2$, silica gel) gave 0.22 g (37% yield) of the desired compound. MS (ES+) m/z 444 (M+H)+.

g) 4-{2-(4-amino-1,2,5-oxadiazol-3-yl)-1-ethyl-7-[(2-thiomorpholinylmethyl)oxy]-1H-imidazo[4,5-c]pyridin-4-yl}-2-methyl-3-butyn-2-ol dihydrochloride (enantiomer E1)

A solution of the compound of 1,1-dimethylethyl 2-({[2-(4-amino-1,2,5-oxadiazol-3-yl)-4-chloro-1-ethyl-1H-imidazo[4,5-c]pyridin-7-yl]oxy}methyl)-4-thiomorpholinecarboxylate enantiomer E1 (0.22 g, 5.00 mmol) in dichloromethane (5 mL) was treated with 4N HCl in dioxane (0.25 mL, 1.00 mmol). After 30 min., the precipitate was isolated by filtration to give 0.21 g (82% yield) of the title compound as a pale yellow solid. MS (ES+) m/z 444 (M+H)+.

Example 4

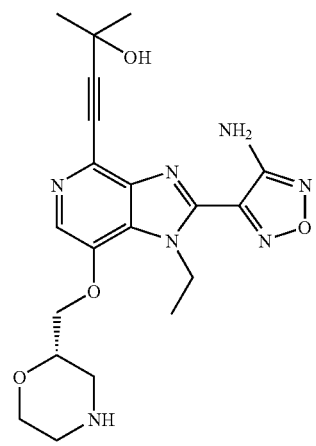

Preparation of 4-(2-(4-amino-1,2,5-oxadiazol-3-yl)-1-ethyl-7-{[(2S)-2-morpholinylmethyl]oxy}-1H-imidazo[4,5-c]pyridin-4-yl)-2-methyl-3-butyn-2-ol a) 2-[(Phenylmethyl)amino]ethyl hydrogen sulfate Chlorosulfonic acid (13.3 mL, 0.2 mol) was added very slowly to (2-[(phenylmethyl)amino]ethanol (30.2 g, 0.2 mol) in carbon tetrachloride (100 mL) in an ice bath. The resulting thick white suspension was stirred at room temperature overnight The suspension was diluted with chloroform and ethanol, warmed to 45° C. and then cooled in an ice bath. The precipitate was collected by filtration, washed with ethanol and dried under vacuum for 16 hrs at 40° C. to afford the desired compound (34 g, 74%). MS (ES)+ m/z 232 [M+H]+.

b) (2S)-4-(Phenylmethyl)-2-{[(phenylmethyl)oxy]methyl}morpholine

The compound of Example 4(a) (28.1 g, 0.116 mol) was added to (2S)-2-{[(phenylmethyl)oxy]methyl}oxirane (19 g, 0.122 mol) in methanol/water (75 mL/75 mL) in an ice bath. Sodium hydroxide (6M, 29 mL) was added over 5 min and once completed the bath was removed and allowed to stir at room temperature for 15 min. The reaction was then stirred at 40° C. in an oil bath for 3 h. The reaction was quickly cooled in an ice bath and sodium hydroxide (28 g, 0.7 mol) and toluene (150 mL) were added. After 10 min, the reaction was heated to 65° C. for 3 hr. After allowing the reaction to cool to RT, the organic layer was separated and the aqueous layer was further extracted with toluene. The combined organic extracts were washed with brine, dried with sodium sulfate, filtered and concentrated in vacuo. The residue was purified by flash chromatography (silica gel, gradient, 15% to 30% ethyl acetate in hexane) to afford the desired compound as an oil (22.4 g, 65%). MS (ES)+ m/e 298 [M+H]+.

c) 1,1-Dimethylethyl (2S)-2-(hydroxymethyl)-4-morpholinecarboxylate

To a solution of the compound of Example 4(b) (22.4 g, 0.075 mol) in ethanol (400 mL) was added 10% palladium on carbon (2.4 g) and trifluoroacetic acid (7.0 mL, 0.09 mol). The mixture was shaken under hydrogen at 50 psi for 24 h. The reaction was filtered and concentrated in vacuo. A solution of potassium carbonate (26 g) in water (260 mL) was added to the residue followed by a solution of di-tert-butyl-dicarbonate (17 g) in ethyl acetate (500 mL). After 1 h, the aqueous layer was removed and the organic layer was washed with brine, dried with sodium sulfate, filtered and concentrated in vacuo. The residue was purified by flash chromatography (silica gel, gradient, 15% to 100% ethyl acetate in hexane) to afford the desired compound as an oil (8 g, 50%). MS (ES)+ m/e 218 [M+H]+.

d) 1,1-Dimethylethyl (2S)-2-(bromomethyl)-4-morpholinecarboxylate 1,1-Dimethylethyl (2S)-2-(hydroxymethyl)-4-morpholinecarboxylate (18.5 g, 0.080 mol) and carbon tetrabromide (34.5 g, 0.104 mol) were dissolved in methylene chloride (400 mL) and cooled in an ice bath. A solution of triphenylphosphine (22 g, 0.084 mol) in methylene chloride (150 ml) was added dropwise over 30 min. After 1 hr at 0° C., the reaction was allowed warm to room temp and was stirred overnight. The reaction volume was reduced by ½ in vacuo and poured onto a pad of silica gel and the product eluted with 15% ethyl acetate in hexane. The filtrate was concentrated in vacuo to afford the desired compound as an oil (12 g, 55%). MS (ES)+ m/e 281 [M+H]+.

e) 1,1-Dimethylethyl (2S)-2-({[2-(4-amino-1,2,5-oxadiazol-3-yl)-4-chloro-1-ethyl-1H-imidazo[4,5-c]pyridin-7-yl]oxy}methyl)-4-morpholinecarboxylate To a solution of the compound of Example 4(d) (10.9 g, 0.039 mol) in dimethylformamide (150 mL) was added intermediate VII (7.8 g, 0.028 mol) and cesium carbonate (11 g, 0.034 mol). After 72 h at 45° C., the reaction was poured into ammonium chloride and water (1.5 L) with stirring. The resulting precipitate was collected by filtration and washed with 1M NaOH and water. The solid was dissolved in tetrahydrofuran and ethyl acetate (hot) and dried with sodium sulfate, filtered and concentrated ½ volume in vacuo and cooled in an ice bath. The resulting precipitate was collected, washed with ethyl acetate and dried under vacuum for 2 h at 40° C. to afford the desired compound (10.2 g, 76%). MS (ES)+ m/e 480 [M+H]+.

f) 1,1-Dimethylethyl (2S)-2-({[2-(4-amino-1,2,5-oxadiazol-3-yl)-1-ethyl-4-(3-hydroxy-3-methyl-1-butyn-1-yl)-1H-imidazo[4,5-c]pyridin-7-yl]oxy}methyl)-4-morpholinecarboxylate A thick-walled pressure vessel was charged under argon with the compound of Example 4(e) (10.1 g, 0.021 mol), 2-methyl-3-butyn-2-ol (10.2 mL, 100 mmol), zinc (0.27 g, 4.2 mmol), sodium iodide (0.63 g, 4.2 mmol), triethylamine (5.8 mL, 0.42 mmol), 1,8-diazabicyclo[5.4.0]undec-7-ene (5.8 mL, 42 mmol), tetrakis(triphenylphosphine) palladium (0) (1.0 g, 0.84 mmol) and dimethylsulfoxide (100 mL). The reaction vessel was sealed and heated at 80° C. for 3 h. After cooling to RT, the reaction was quenched by pouring into sat. ammonium chloride (1 L) and stirred for 30 min. The solid was collected by filtration. Purification by flash chromatography (silica gel, gradient, 1% to 10% methanol in chloroform) gave the desired compound as a solid (10.5 g, 95%). MS (ES)+ m/z 528 [M+H]+.

g) 4-(2-(4-Amino-1,2,5-oxadiazol-3-yl)-1-ethyl-7-{[(2S)-2-morpholinylmethyl]oxy}-1H-imidazo[4,5-c]pyridin-4-yl)-2-methyl-3-butyn-2-ol To a suspension of 1,1-Dimethylethyl (2S)-2-({[2-(4-amino-1,2,5-oxadiazol-3-yl)-1-ethyl-4-(3-hydroxy-3-methyl-1-butyn-1-yl)-1H-imidazo[4,5-c]pyridin-7-yl]oxy}methyl)-4-morpholinecarboxylate (14.2 g, 0.027 mol) in methylene chloride (150 mL) was added trifluoroacetic acid (40 mL). After 1 h, the solvent was removed in vacuo. The residue was evaporated from ethyl acetate (2×) to give a solid. The residue was suspended in water and treated with 1N NaOH in an ice bath until the mixture was basic (pH 8). The precipitate was isolated by filtration, washed with water, ethyl acetate and dried in a vacuum oven at 40° C. for 4 h. The resulting solid was treated with ethyl acetate (250 ml) and stirred at 65° C. then allowed to cool to RT and then placed in an ice bath and then filtered and the solid dried in a vacuum oven at 40° C. The resulting solid was suspended in 20% tetrahydrofuran/ethanol (1.2 L). Darco G60 activated charcoal (3.9 g) was added and the mixture heated at reflux for 90 min. and filtered while hot through celite. The solvent was removed and retreated with ethanol and removed in vacuo (2×). The resulting solid was dried under high vacuum for 24 hr at 40° C. to afford the title compound (7.24 g, 64%). MS (ES)+ m/e 428 [M+H]+.

Example 5

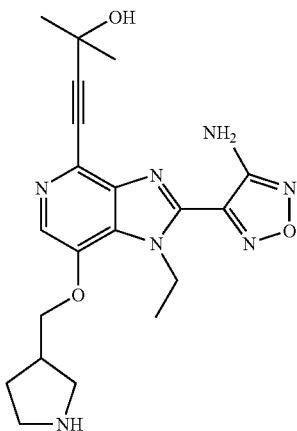

Preparation of 4-{2-(4-amino-1,2,5-oxadiazol-3-yl)-1-ethyl-7-[(3-Pyrrolidinylmethyl)oxy]-1H-imidazo[4,5-c]pyridin-4-yl}-2-methyl-3-butyn-2-ol, bis-trifluoroacetic acid salt a) 1,1-Dimethylethyl 3-(bromomethyl)-1-pyrrolidinecarboxylate To a solution of 1,1-dimethylethyl 3-(hydroxymethyl)-1-pyrrolidinecarboxylate (0.56 g, 2.8 mmol) with carbon tetrabromide (1.39 g, 4.2 mmol) in methylene chloride (10 mL) was added drop wise a solution of triphenyl phosphine (0.73 g, 2.8 mmol in 5 mL of methylene chloride). Upon completion the mixture was stirred 18 h at room temperature. The solvent was removed at reduced pressure and the residue stirred in 10% ethyl acetate 90% hexane. The mixture was filtered and the resulting solution chromatographed on silica eluting with a gradient of 0-25% EtOAc in hexane to afford the desired compound (0.41 g, 55%). MS (ES+) m/z 264 (M+H)+.

b) 1,1-Dimethylethyl 3-({[2-(4-amino-1,2,5-oxadiazol-3-yl)-4-chloro-1-ethyl-1H-imidazo[4,5-c]pyridin-7-yl]oxy}methyl)-1-pyrrolidinecarboxylate A mixture consisting of intermediate VII (100 mg, 0.35 mmol) in DMF (2 mL) with cesium carbonate (290 mg, 0.9 mmol) and the compound of Example 5(a) (290 mg, 1.1 mmol) was stirred at room temperature for 24 h. The mixture was poured into rapidly stirring ice water (7 mL) and stirring continued for 10 min. To this was added cyclohexane (7 mL) and stirring continued for an additional 20 min. The solid was collected by filtration then washed with cyclohexane and dried in vacuo to afford the desired compound (111 mg, 69%). MS (ES+) m/z 464 (M+H)+.

c) 1,1-Dimethylethyl 3-({[2-(4-amino-1,2,5-oxadiazol-3-yl)-1-ethyl-4-(3-hydroxy-3-methyl-1-butyn-1-yl)-1H-imidazo[4,5-c]pyridin-7-yl]oxy}methyl)-1-pyrrolidinecarboxylate In a thick walled pressure vessel was charged with the compound of Example 5(b) (100 mg, 0.22 mmol), 2-methyl-3-butyn-2-ol (0.25 mL, 2.6 mmol), (Ph$_3$P)$_4$Pd (30 mg), diisopropyl amine (0.4 mL) and dioxane (4 mL). The vessel was sealed and stirred under an argon atmosphere at 100° C. for 6 h. The mixture was concentrated at reduced pressure then triturated with ethyl acetate (4 mL) to afford the desired compound (82 mg, 75%). MS (ES+) m/z 512 (M+H)+.

d) 4-{2-(4-Amino-1,2,5-oxadiazol-3-yl)-1-ethyl-7-[(3-pyrrolidinylmethyl)oxy]-1H-imidazo[4,5-c]pyridin-4-yl}-2-methyl-3-butyn-2-ol, bis-trifluoroacetic acid salt The compound of Example 5(c) (75 mg, 0.15 mmol) was stirred in a 20% solution of TFA in methylene chloride (3 mL) at room temperature for 20 min. Toluene (3 mL) was added and all volatiles removed at reduced pressure. The residue was purified by preparative reversed phase HPLC to afford the title compound as the di-TFA salt (40 mg, 43%). MS (ES+) m/z 412 (M+H)+.

Example 6

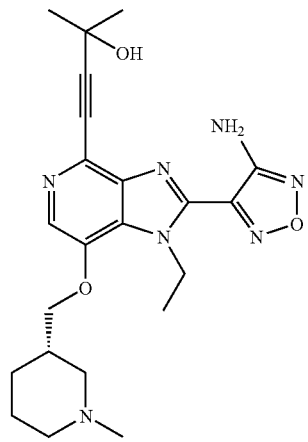

Preparation of 4-[2-(4-amino-1,2,5-oxadiazol-3-yl)-1-ethyl-7-({[(3S)-1-methyl-3-piperidinyl]methyl}oxy)-1H-imidazo[4,5-c]pyridin-4-yl]-2-methyl-3-butyn-2-ol, dihydrochloride a) [(3S)-1-Methyl-3-piperidinyl]methanol To a stirred solution of lithium aluminum hydride (10.5 ml of 1M solution in THF, 10.5 mmol) in ether (15 mL) at 20° C. was added dropwise a solution of 1,1-dimethylethyl (3S)-3-(hydroxymethyl)-1-piperidinecarboxylate (1.50 g, 7.0 mmol) in THF (5 mL). After 1.5 h at room temperature, water (0.4 mL) was added followed by 15% aqueous sodium hydroxide solution (0.4 mL) then water (1.2 mL). This was stirred 20 min then filtered. The filtrate was concentrated under reduced pressure to give 0.87 g used in the next step without further purification. MS (ES+) m/z 130.2 (M+H)+.

b) 4-[4-Chloro-1-ethyl-7-({[(3S)-1-methyl-3-piperidinyl]methyl}oxy)-1H-imidazo[4,5-c]pyridin-2-yl]-1,2,5-oxadiazol-3-amine To a stirred mixture consisting of compound of Example 6(a) (0.260 g, 2 mmol) with triphenyl phosphine polymer bound (1.56 g of 1.6 mmol/g polymer, 2.5 mmol) in methylene chloride (35 mL) at 0° C. was added a dropwise a solution of diethyl azodicarboxylate (0.33 mL, 2.2 mmol) in methylene chloride (5 mL). The cooling bath was removed and stirring continued for 20 min. To this mixture at room temperature was added a solution of the compound of intermediate VII (280 mg, 1 mmol) in THF (40 mL). The mixture was stirred 18 h at room temperature then filtered and to the filtrate was added ethyl acetate (60 mL). The resulting solution was washed with water (50 mL) then brine (50 mL). The organic extract was dried over MgSO$_4$, filtered and the solvent removed under reduced pressure to give 0.40 g crude solid that was used in the next step without further purification. MS (ES+) m/z 392.3 (M+H)$^+$.

c) 4-[2-(4-Amino-1,2,5-oxadiazol-3-yl)-1-ethyl-7-({[(3S)-1-methyl-3-piperidinyl]methyl}oxy)-1H-imidazo[4,5-c]pyridin-4-yl]-2-methyl-3-butyn-2-ol dihydrochloride salt A thick-walled pressure vessel was charged with the compound of Example 1(b) (0.140 g, 0.35 mmol), Zn dust (0.004 g, 0.06 mmol), NaI (0.008 g, 0.0.05 mmol), DBU (0.08 mL, 0.54 mmol), TEA (0.075 mL, 0.53 mmol), 2-methyl-3-butyn-2-ol (0.07 mL, 0.75 mmol) and (Ph$_3$P)$_4$Pd (0.015 g, 0.013 mmol) in DMSO (2 mL). The mixture was poured into rapidly stirring water (10 mL) with ethyl acetate (5 mL) and cyclohexane (5 mL). The resulting solid was collected then crystallized from ethanol. The crystalline solid was dissolved in hot ethanol then HCl (0.175 mL of 4M solution in dioxane 0.70 mmol) was added. The precipitate was collected and dried under reduced pressure to afford the title compound (0.148 g) MS (ES+) m/z 440.3 (M+H)$^+$.

Example 7

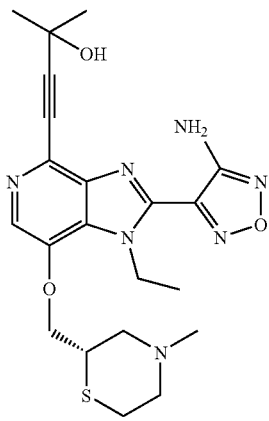

Preparation of 4-(2-(4-amino-1,2,5-oxadiazol-3-yl)-1-ethyl-7-{[(4-methyl-2-thiomorpholinyl)methyl]oxy}-1H-imidazo[4,5-c]pyridin-4-yl)-2-methyl-3-butyn-2-ol (enantiomer E1)

To a solution of 4-{2-(4-amino-1,2,5-oxadiazol-3-yl)-1-ethyl-7-[(2-thiomorpholinylmethyl)oxy]-1H-imidazo[4,5-c]pyridin-4-yl}-2-methyl-3-butyn-2-ol (enantiomer E1) (0.88 g, 1.98 mmol) in MeOH (38 mL) at 0° C. was added NaCNBH$_3$ (0.14 g, 2.20 mmol) and acetic acid (0.57 mL). This was followed by dropwise addition of formaldehyde (0.25 mL). The reaction was allowed to warm to RT. After 18 h, the reaction was poured into 50% aq. NaHCO$_3$. The solution was cooled to 0° C. and the resultant precipitate was collected to give 0.90 g of the desired compound. MS (ES+) m/z 458.4 (M+H)$^+$.

Example 8

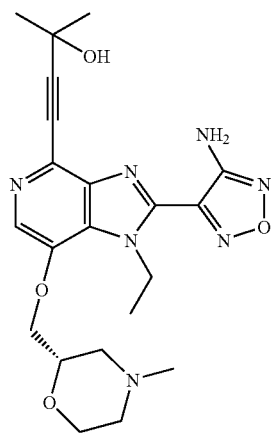

Preparation of 4-[2-(4-amino-1,2,5-oxadiazol-3-yl)-1-ethyl-7-({[(2S)-4-methyl-2-morpholinyl]methyl}oxy)-1H-imidazo[4,5-c]pyridin-4-yl]-2-methyl-3-butyn-2-ol To 4-(2-(4-amino-1,2,5-oxadiazol-3-yl)-1-ethyl-7-{[(2S)-2-morpholinylmethyl]oxy}-1H-imidazo[4,5-c]pyridin-4-yl)-2-methyl-3-butyn-2-ol (0.13 g, 0.30 mmol) suspended in methanol (2 mL) was added formaldehyde (37% in water, 0.045 mL, 0.6 mmol). After 5 min, acetic acid (0.051 mL, 0.9 mmol) was added following by sodium triacetoxyborohydride (0.16 g, 0.75 mmol). After 1 h. the solvent was removed in vacuo and the residue suspended in 1N NaOH and extracted with ethyl acetate/tetrahydrofuran. The combined organic extracts were washed with brine and dried sodium sulfate. The filtrate was concentrated in vacuo to afford the desired compound as a solid (0.10 g, 77%) MS (ES+) m/z 442 [M+H]⁺.

Example 9

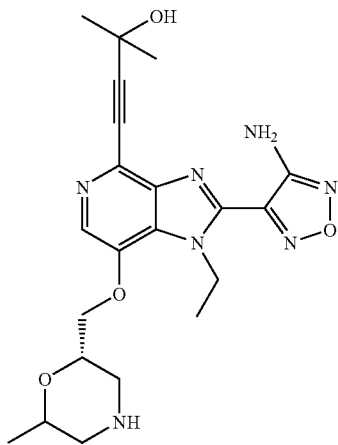

Preparation of 4-[2-(4-amino-1,2,5-oxadiazol-3-yl)-1-ethyl-7-({[(2R)-6-methyl-2-morpholinyl]methyl}oxy)-1H-imidazo[4,5-c]pyridin-4-yl]-2-methyl-3-butyn-2-ol, dihydrochloride a) (2S)-1-({[2,4-Bis(methyloxy)phenyl]methyl}amino)-3-[(phenylmethyl)oxy]-2-propanol To a stirred solution of 2,4-dimethoxybenzylamine (1.00 g, 5.99 mmol) in MeOH (30 mL) at room temperature was added benzyl(S)-(+)-glycidyl ether (0.88 g, 5.40 mmol). After 12 h the reaction was concentrated in vacuo. The residue was dissolved in ethyl acetate (75 mL) and washed sequentially with 1 N HCl (25 mL) and brine (25 mL). The solution was dried over MgSO₄, filtered and the solvent removed under reduced pressure to give 1.35 g of the crude oil that was used in the next step without further purification. MS (ES+) m/z 332.2 (M+H)⁺.

b) N-{[2,4-Bis(methyloxy)phenyl]methyl}-2-bromo-N-{(2R)-2-hydroxy-3-[(phenylmethyl)oxy]propyl}propanamide To a stirred solution of the compound of Example 9(a) (0.50 g, 1.50 mmol) and triethylamine (0.25 mL, 3.0 mmol) in CH₂Cl₂ (30 mL) at 0° C. was added 2-bromopropionyl chloride (0.280 g, 1.65 mmol). After 12 h at room temperature, the solvent was removed under reduced pressure. The residue was dissolved in ethyl acetate (75 mL) and washed sequentially with 1 N HCl (25 mL) and brine (25 mL). The solution was dried over MgSO₄, filtered and the solvent removed under reduced pressure to give 0.51 g of the crude oil that was used in the next step without further purification. MS (ES+) m/z 467.2 (M+H)⁺.

c) (6R)-4-{[2,4-Bis(methyloxy)phenyl]methyl}-2-methyl-6-{[(phenylmethyl)oxy]methyl}-3-morpholinone A mixture of the compound of Example 9(b) (0.40 g, 0.86 mmol) and sodium hydride (0.067 g, 1.37 mmol) in THF (15 mL) was stirred under nitrogen at room temperature for 16 h. The reaction was diluted with ethyl acetate (50 mL) washed with water (3×15 mL) and brine (20 mL). The solution was dried over MgSO₄, filtered and the solvent removed under reduced pressure to give the desired product. Preparative HPLC(YMC-Pack ODS-A column, 30 mm i.d.×75 mm, 20 mL/min, gradient, A: water-0.1% trifluoroacetic acid, B: acetonitrile-0.1% trifluoroacetic acid, 10-90% acetonitrile during 12 min, UV detection at 254 nm) gave 0.245 g (74% yield) of the title compound. MS (ES+) m/z 386.2 (M+H)⁺.

d) (6R)-4-{[2,4-Bis(methyloxy)phenyl]methyl}-2-methyl-6-{[(phenylmethyl)oxy]methyl}morpholine A solution of the compound of Example 9(c) (0.200 g, 0.51 mmol) in THF was added LAH (1M, 0.60 mL) at 0° C. under nitrogen. The reaction was warmed to ambient temperature and stirred for 12 h. To the reaction was added water (0.02 mL), slowly at 0° C. and 1N NaOH (0.02 mL), the mixture was allowed to stir at room temperature for 1 h. Additional water (0.07 mL) was added and stirred for 30 min. The mixture was filtered. The solids were washed several times with ethyl acetate. The filtrate was concentrated under reduced pressure to give 0.12 g of the crude oil that was used in the next step without further purification. MS (ES+) m/z 372.2 (M+H)⁺.

e) (6R)-2-Methyl-6-{[(phenylmethyl)oxy]methyl}morpholine

A solution of the compound of Example 9(d) (0.12 g, 0.32 mmol) in CH₂Cl₂ (5 mL) at ambient temperature was treated with 1-chloroethyl chloroformate (0.10 mL, 1.4 mmol). The reaction was stirred at refluxed for 2 h, the solvent was removed under reduced pressure to give a crude residue. The residue was dissolved in MeOH (5 mL) and stirred at refluxed for 1 h. The solvent was removed under reduced pressure to give a crude residue 0.51 g of the crude oil that was used in the next step without further purification. MS (ES+) m/z 222.2 (M+H)⁺.

f) 1,1-Dimethylethyl (6R)-2-methyl-6-{[(phenylmethyl)oxy]methyl}-4-morpholinecarboxylate A solution of the compound of Example 9(e) (0.20 g, 0.90 mmol) in CH₃CN (5 mL) at ambient temperature was treated with di-tert-butyl dicarbonate (0.22 g, 1.0 mmol). Removal of the organics gave the crude residue. Preparative HPLC (YMC-Pack ODS-A column, 30 mm i.d.×75 mm, 20 mL/min, gradient, A: water-0.1% trifluoroacetic acid, B: acetonitrile-0.1% trifluoroacetic acid, 10-90% acetonitrile during 12 min, UV detection at 254 nm) gave 0.214 g (79% yield) of the title compound. MS (ES+) m/z 322.2 (M+H)⁺.

g) 1,1-Dimethylethyl (2R)-2-(hydroxymethyl)-6-methyl-4-morpholinecarboxylate A solution of the compound of Example 9(f) (0.20 g, 0.62 mmol) in EtOH (5 mL) was treated with palladium hydroxide (0.10 g). The mixture was placed in a Parr apparatus and shaken for 16 h under 55 psi of H₂ atmosphere. The mixture was filtered over a pad of Celite and washed with MeOH (25 mL). The filtrate was concentrated under reduced pressure to give 0.15 g of the crude oil that was used in the next step without further purification. MS (ES+) m/z 232.2 (M+H)⁺.

h) 1,1-Dimethylethyl (6R)-2-methyl-6-({[(4-methylphenyl)sulfonyl]oxy}methyl)-4-morpholinecarboxylate A solution of the compound of Example 9(g) (0.15 g, 0.65 mmol) in CH$_2$Cl$_2$ (5 mL) was added triethylamine (0.10 mL), dimethylaminopyridine (0.02 g) and tosyl chloride (0.15 g, 0.79 mmol). After 12 h the reaction was concentrated in vacuo. The residue was dissolved in ethyl acetate (75 mL) and washed sequentially with 1 N HCl (25 mL) and brine (25 mL). The solution was dried over MgSO$_4$, filtered and the solvent removed under reduced pressure to give of the crude residue. The crude residue was subjected to flash chromatography (25-100% EtOAc/Hex, silica gel) to give 0.14 g of the desired compound as light yellow solid. MS (ES+) m/z 286.2 (M+H−BOC)$^+$, no parent ion was observed.

i) 1,1-Dimethylethyl (2S)-2-({[2-(4-amino-1,2,5-oxadiazol-3-yl)-4-chloro-1-ethyl-1H-imidazo[4,5-c]pyridin-7-yl]oxy}methyl)-6-methyl-4-morpholinecarboxylate A mixture of the compound of Example 9(h) (0.14 g, 0.36 mmol), the compound of intermediate VII (0.11 g, 0.40 mmol), and cesium carbonate (0.20 g, 0.55 mmol) in DMF (9 mL) was stirred under nitrogen at 50° C. for 16 h. After allowing the reaction to cool to ambient temperature, the mixture was diluted with ethyl acetate (50 mL) washed with water (3×15 mL) and brine (20 mL). The solution was dried over MgSO$_4$, filtered and the solvent removed under reduced pressure to give the desired product. Preparative HPLC (YMC-Pack ODS-A column, 30 mm i.d.×75 mm, 20 mL/min, gradient, A: water-0.1% trifluoroacetic acid, B: acetonitrile-0.1% trifluoroacetic acid, 10-90% acetonitrile during 12 min, UV detection at 254 nm) gave 0.124 g (70% yield) of the title compound as a white solid. MS (ES+) m/z 494.2 (M+H)$^+$.

j) 1,1-Dimethylethyl (2S)-2-({[2-(4-amino-1,2,5-oxadiazol-3-yl)-1-ethyl-4-(3-hydroxy-3-methyl-1-butyn-1-yl)-1H-imidazo[4,5-c]pyridin-7-yl]oxy}methyl)-6-methyl-4-morpholinecarboxylate A thick-walled pressure vessel was charged with the compound of Example 9(i) (0.124 g, 0.25 mmol), Zn dust (0.02 g, 0.30 mmol), NaI (0.04 g, 0.27 mmol), DBU (0.20 mL, 1.32 mmol), TEA (0.15 mL, 1.07 mmol), 2-methyl-3-butyn-2-ol (0.20 mL, 2.07 mmol) and (Ph$_3$P)$_4$Pd (0.04 g, 0.03 mmol) in DMSO (5 mL). After purging with nitrogen for 10 min., the reaction vessel was sealed and heated at 80° C. for 3 h. The reaction mixture was diluted with water and extracted with ethyl acetate. The organic extracts were washed with water, brine and dried over sodium sulfate. The solvent was removed under reduced pressure to afford a light yellow residue. The crude residue was subjected to flash chromatography (0-10% MeOH/CHCl3, silica gel) to give an additional 0.10 g of the desired compound as light yellow solid. MS (ES+) m/z 541 (M+H)$^+$.

k) 4-[2-(4-Amino-1,2,5-oxadiazol-3-yl)-1-ethyl-7-({[(2S)-6-methyl-2-morpholinyl]methyl}oxy)-1H-imidazo[4,5-c]pyridin-4-yl]-2-methyl-3-butyn-2-ol dihydrochloride salt A solution of the compound of Example 9(j) (0.10 g, 0.18 mmol) in methanol (5 mL) was added 4N HCl in 1,4-dioxane (3.5 mL, 16.0 mmol). After 3 h at ambient temperature, the solvent was removed under reduced pressure. The residue was triturated with dichloromethane and the solid was collected by filtration to give 0.063 g of the title compound as light yellow solid. MS (ES+) m/z 441 (M+H)$^+$.

Example 10

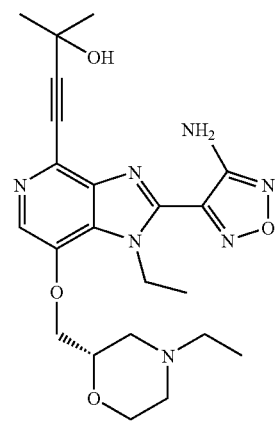

Preparation of 4-[2-(4-amino-1,2,5-oxadiazol-3-yl)-1-ethyl-7-({[(2S)-4-ethyl-2-morpholinyl]methyl}oxy)-1H-imidazo[4,5-c]pyridin-4-yl]-2-methyl-3-butyn-2-ol To a solution of the compound of Example 4 (0.13 g, 0.30 mmol) in MeOH (4 mL) at 0° C. was added acetaldehyde (0.034 mL, 0.61 mmol) and acetic acid (0.052 mL. 0.90 mmol). This was followed by the addition of NaCNBH3 (0.048 g, 0.76 mmol). The reaction was allowed to warm to RT. After 18 h, the reaction was poured into 50% aq. NaHCO$_3$. The solution was cooled to 0° C. and the resultant precipitate was collected to give 0.10 g of the desired compound. MS (ES+) m/z 456.4 (M+H)$^+$.

Example 11

Capsule Composition

An oral dosage form for administering the present invention is produced by filing a standard two piece hard gelatin capsule with the ingredients in the proportions shown in Table I, below.

TABLE I

| INGREDIENTS | AMOUNTS |
|---|---|
| 4-(2-(4-amino-1,2,5-oxadiazol-3-yl)-1-ethyl-7-{[(3S)-3-piperidinylmethyl]oxy}-1H-imidazo[4,5-c]pyridin-4-yl)-2-methyl-3-butyn-2-ol | 25 mg |
| Lactose | 55 mg |
| Talc | 16 mg |
| Magnesium Stearate | 4 mg |

Example 12

Injectable Parenteral Composition

An injectable form for administering the present invention is produced by stirring 1.5% by weight of 4-(2-(4-amino-1,2,5-oxadiazol-3-yl)-1-ethyl-7-{[(2S)-2-thiomorpholinylmethyl]oxy}-1H-imidazo[4,5-c]pyridin-4-yl)-2-methyl-3-butyn-2-ol, in 10% by volume propylene glycol in water.

Example 13

Tablet Composition

The sucrose, calcium sulfate dihydrate and an Akt inhibitor as shown in Table II below, are mixed and granulated in the proportions shown with a 10% gelatin solution. The wet granules are screened, dried, mixed with the starch, talc and stearic acid, screened and compressed into a tablet.

TABLE II

| INGREDIENTS | AMOUNTS |
| --- | --- |
| 4-(2-(4-amino-1,2,5-oxadiazol-3-yl)-1-ethyl-7-{[(2S)-2-thiomorpholinylmethyl]oxy}-1H-imidazo[4,5-c]pyridin-4-yl)-2-methyl-3-butyn-2-ol, dihydrochloride | 20 mg |
| calcium sulfate dehydrate | 30 mg |
| Sucrose | 4 mg |
| Starch | 2 mg |
| Talc | 1 mg |
| stearic acid | 0.5 mg |

While the preferred embodiments of the invention are illustrated by the above, it is to be understood that the invention is not limited to the precise instructions herein disclosed and that the right to all modifications coming within the scope of the following claims is reserved.

What is claimed is:

1. A compound selected from:
   4-(2-(4-amino-1,2,5-oxadiazol-3-yl)-1-ethyl-7-{[(3S)-3-piperidinylmethyl]oxy}-1H-imidazo[4,5-c]pyridin-4-yl)-2-methyl-3-butyn-2-ol;
   4-(2-(4-amino-1,2,5-oxadiazol-3-yl)-1-ethyl-7-{[(2S)-2-thiomorpholinylmethyl]oxy}-1H-imidazo[4,5-c]pyridin-4-yl)-2-methyl-3-butyn-2-ol;
   4-(2-(4-amino-1,2,5-oxadiazol-3-yl)-1-ethyl-7-{[(2S)-2-morpholinylmethyl]oxy}-1H-imidazo[4,5-c]pyridin-4-yl)-2-methyl-3-butyn-2-ol; and
   4-[2-(4-amino-1,2,5-oxadiazol-3-yl)-1-ethyl-7-({[(2R)-6-methyl-2-morpholinyl]methyl}oxy)-1H-imidazo[4,5-c]pyridin-4-yl]-2-methyl-3-butyn-2-ol;
   and/or a pharmaceutically acceptable salt thereof.

2. A compound of claim 1 that is:
   4-(2-(4-amino-1,2,5-oxadiazol-3-yl)-1-ethyl-7-{[(3S)-3-piperidinylmethyl]oxy}-1H-imidazo[4,5-c]pyridin-4-yl)-2-methyl-3-butyn-2-ol;
   and/or a pharmaceutically acceptable salt thereof.

3. A compound of claim 1 that is:
   4-(2-(4-amino-1,2,5-oxadiazol-3-yl)-1-ethyl-7-{[(2S)-2-thiomorpholinylmethyl]oxy}-1H-imidazo[4,5-c]pyridin-4-yl)-2-methyl-3-butyn-2-ol;
   and/or a pharmaceutically acceptable salt thereof.

4. A compound of claim 1 that is:
   4-(2-(4-amino-1,2,5-oxadiazol-3-yl)-1-ethyl-7-{[(2S)-2-morpholinylmethyl]oxy}-1H-imidazo[4,5-c]pyridin-4-yl)-2-methyl-3-butyn-2-ol;
   and/or a pharmaceutically acceptable salt thereof.

5. A compound of claim 1 that is:
   4-[2-(4-amino-1,2,5-oxadiazol-3-yl)-1-ethyl-7-({[(2R)-6-methyl-2-morpholinyl]methyl}oxy)-1H-imidazo[4,5-c]pyridin-4-yl]-2-methyl-3-butyn-2-ol;
   and/or a pharmaceutically acceptable salt thereof.

6. A pharmaceutical composition comprising a compound according to claim 1 and a pharmaceutically acceptable carrier.

7. A pharmaceutical composition comprising a compound according to claim 2 and a pharmaceutically acceptable carrier.

8. A process for preparing a pharmaceutical composition containing a pharmaceutically acceptable carrier and an effective amount of a compound of claim 1, which process comprises mixing the compound of claim 1 and a pharmaceutically acceptable carrier.

9. A compound of claim 1 that is:
   4-(2-(4-amino-1,2,5-oxadiazol-3-yl)-1-ethyl-7-{[(3S)-3-piperidinylmethyl]oxy}-1H-imidazo[4,5-c]pyridin-4-yl)-2-methyl-3-butyn-2-ol.

10. A compound of claim 1 that is:
    4-(2-(4-amino-1,2,5-oxadiazol-3-yl)-1-ethyl-7-{[(2S)-2-thiomorpholinylmethyl]oxy}-1H-imidazo[4,5-c]pyridin-4-yl)-2-methyl-3-butyn-2-ol.

11. A compound of claim 1 that is:
    4-(2-(4-amino-1,2,5-oxadiazol-3-yl)-1-ethyl-7-{[(2S)-2-morpholinylmethyl]oxy}-1H-imidazo[4,5-c]pyridin-4-yl)-2-methyl-3-butyn-2-ol.

12. A compound of claim 1 that is:
    4-[2-(4-amino-1,2,5-oxadiazol-3-yl)-1-ethyl-7-({[(2R)-6-methyl-2-morpholinyl]methyl}oxy)-1H-imidazo[4,5-c]pyridin-4-yl]-2-methyl-3-butyn-2-ol.

13. A pharmaceutical composition comprising 4-(2-(4-amino-1,2,5-oxadiazol-3-yl)-1-ethyl-7-{[(3S)-3-piperidinylmethyl]oxy}-1H-imidazo[4,5-c]pyridin-4-yl)-2-methyl-3-butyn-2-ol and a pharmaceutically acceptable carrier.

* * * * *

SEQUENCE LISTING

```
<160> NUMBER OF SEQ ID NOS: 5

<210> SEQ ID NO 1
<211> LENGTH: 12
<212> TYPE: DNA
<213> ORGANISM: Artificial Sequence
<220> FEATURE:
<223> OTHER INFORMATION: Primer

<400> SEQUENCE: 1
arkrraysgh ha                                                     12

<210> SEQ ID NO 2
<211> LENGTH: 26
<212> TYPE: DNA
<213> ORGANISM: Artificial Sequence
<220> FEATURE:
<223> OTHER INFORMATION: Primer

<400> SEQUENCE: 2
tatataggat ccatgagcga cgtggc                                      26

<210> SEQ ID NO 3
<211> LENGTH: 29
<212> TYPE: DNA
<213> ORGANISM: Artificial Sequence
<220> FEATURE:
<223> OTHER INFORMATION: AKT1 Mutagenic Primer

<400> SEQUENCE: 3
aaatttctcg agtcaggccg tgctgctgg                                   29

<210> SEQ ID NO 4
<211> LENGTH: 25
<212> TYPE: DNA
<213> ORGANISM: Artificial Sequence
<220> FEATURE:
<223> OTHER INFORMATION: Selection Primer

<400> SEQUENCE: 4
acctggcggc cacgctactt cctcc                                       25

<210> SEQ ID NO 5
<211> LENGTH: 23
<212> TYPE: DNA
<213> ORGANISM: Artificial Sequence
<220> FEATURE:
```

-continued

```
<223> OTHER INFORMATION: Biotinylated synthetic peptide

<400> SEQUENCE: 5
ctcgagcatg caactagagg gcc                                              23
```